(12) United States Patent
Bradley et al.

(10) Patent No.: US 6,852,747 B2
(45) Date of Patent: Feb. 8, 2005

(54) RESORCINOL DERIVATIVES

(75) Inventors: Stuart E. Bradley, Birmingham (GB); Eric W. Collington, Knebworth (GB); Matthew C. Fyfe, Birmingham (GB); Martin J. Procter, Walsall (GB); Colin P. Sambrook Smith, Kenilworth (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/446,062

(22) Filed: May 27, 2003

(65) Prior Publication Data

US 2003/0180236 A1 Sep. 25, 2003

Related U.S. Application Data

(62) Division of application No. 09/949,026, filed on Sep. 7, 2001, now Pat. No. 6,590,105.
(60) Provisional application No. 60/231,623, filed on Sep. 11, 2000.

(51) Int. Cl.$^7$ .................... C07D 257/04; C07D 311/13; A61K 31/381

(52) U.S. Cl. ................. 514/381; 514/602; 424/401

(58) Field of Search ................. 514/381, 602; 424/401, 78.03

(56) References Cited

U.S. PATENT DOCUMENTS

| 4,526,179 A | 7/1985 | Salesky |
| 4,959,393 A | 9/1990 | Torihara et al. |
| 5,449,518 A | 9/1995 | Junin et al. |
| 5,508,155 A | 4/1996 | Marrese et al. |
| 5,580,549 A | 12/1996 | Fukuda et al. |
| 6,123,959 A | 9/2000 | Jones et al. |
| 6,132,740 A | 10/2000 | Hu |
| 6,159,482 A | 12/2000 | Tuloup et al. |

FOREIGN PATENT DOCUMENTS

| WO | WO 99/12474 A | 3/1999 |
| WO | WO 00/56702 A | 9/2000 |

OTHER PUBLICATIONS

J.A. Beavo, Physiol. Rev., 1995, pp 725–748, vol. 75.
T.L. Fink, et al., "Expression of an Active, Monomeric Catalytic Domain of the cGMP–binding cGMP–specific Phosphodiesterase (PDE5)", J. Biol. Chem., Dec. 3, 1999, pp 34,613–34,620, vol. 274, No. 49.
J Lim, et al., "Activation of the cAMP–specific Phosphodiesterase PDE4D3 by Phosphorylation" J. Biol. Chem., Jul. 9, 1999, pp 29677–19685, vol. 274, No. 28.
S.L.C. Jin, et al., "Characterization of the Structure of a Low Km, Rolipram–sensitive cAMP Phosphodiesterase", J. Biol. Chem., Sep. 15, 1992, pp 18929–18939, vol. 267, No. 26.

T. Kovala, et al., "Recombinant Expression of a Type IV, cAMP–Specific Phosphodiesterase: Characterization and Structure–Function Studies of Deletion Mutants", Biochem., 1997, pp 2968–2976, vol. 36.
T. Michaeli, et al., "Isolation and Characterization of a Previously Undetected Human cAMP Phosphodiesterase by Complementation of CAMP Phosphodiesterase–deficient Saccharomyces cereuisiae", J. Biol. Chem., Jun. 15, 1993, pp 12925–12932, vol. 268, No. 17.
W.K. Sonnenburg, et al., "Identification of Inhibitory and Calmodulin–binding Domains of the PDE1A1 and PDE1A2 Calmodulin–stimulated Cyclic Nucleotide Phosphodiesterases", J. Biol. Chem., Dec. 29, 1995, pp 30989–31000, vol. 270, No. 52.
Y Kenan, et al., "Functions of the N–terminal Region of Cyclic Nucleotide Phosphodiesterase 3 (PDE 3) Isoforms", J. Biol. Chem., Apr. 21, 2000, pp 12331–12338, vol. 275, No. 16.
Wolfgang Baehr, et al. "Isolation and Characterization of cGMP Phosphodiesterase from Bovine Rod Outer Segments", J. Biol. Chem., Nov. 25, 1979, pp 11669–11677, vol. 254, No. 22.
J. A. Beavo, et al., "Hydrolysis of Cyclic Guanosine and Adenosine 3',5'–Monophosphates by Rat and Bovine Tissues", J. Biol. Chem., Nov. 10, 1970, pp 5649–5655, vol. 245, No. 21.
Timothy J. Bloom, et al., "Identification and Tissue–specific Expression of PDE7 Phosphodiesterase Splice Variants", Proc. Natl. Acad. Sci. USA, Nov. 1996, pp 14188–14192, vol. 93.
Bernard K. K. Fung, et al., "Subunit Stoichiometry of Retinal Rod cGMP Phosphodiestrase", Biochem., 1990, pp 2657–2664, vol. 29.
Clare Gardner, et al., "Cloning and Characterization of the Human adn Mouse PDE7B, a Novel cAMP–Specific Cyclic Nucleotide Phosphodiestrase", Biochem. Biophys.Res. Commun., 2000, pp 186–192, vol. 272.
Ping Han, et al., Alternative Splicing of the High Affinity cAMP–Specific Phosphodiesterase (PDE7A) mRNA in Human Skeletal Muscle and Heart, J. Biol. Chem., Jun. 6, 1997, pp 16152–16157, vol. 272, No. 26.
Ralf Hoffmann, et al., Differential Distribution of Rat PDE–7 mRNA in Embryonic and Adult Rat Brain, Cell Biochem. Biophys., 1998, pp 103–113, vol. 28.
Michio Ichimura, et al., "A new Cyclic Nucleotide Phosphodiesterase Isozyme Expressed ion the T–Lymphocyte Cell Lines", Biochem. Biophys. Res Commun., Jun. 30, 1993, vol. 193, No. 3.

(List continued on next page.)

*Primary Examiner*—Joseph K. McKane
*Assistant Examiner*—Rebecca Anderson
(74) *Attorney, Agent, or Firm*—Roseanne Goodman

(57) ABSTRACT

The present invention relates to certain resorcinol derivatives and their use as skin lightening agents.

9 Claims, No Drawings

OTHER PUBLICATIONS

Carolyn J. Smith, et al., "Hormone-sensitive Cyclic GMP-inhibited Cyclic AMP Phosphodiesterase in Rat Adipocytes", J. Biol. Chem., Jul. 15, 1991, pp 13385–13390, vol. 266, No. 20.

Theodore J. Torphy, et al., "Biochemical Characterostocs and Cellular Regulation of Phosphodiesterase IV", New Drugs in Allergy and Asthma, 1993, pp 51–71, Agents & Actions Suuplement vol. 43.

Genbank Accession No: U77880; Rattus norvegicus GI:1916748; Sep. 28, 2001.

Genbank Accession No: AJ251860 Homo sapiens mRNA GI:8216982; May 24, 2000.

Genbank Accession No: LI2052 Homo sapiens cAMP GI:179892; Jul. 22, 1999.

Genbank Accession No: U68171 Mus musculus cycl GI:1549394; Sep. 18, 1996.

Genbank Accession No: U67932 Homo sapiens cAMP GI:2306763; Jul. 22, 1999.

RESORCINOL DERIVATIVES

This application is a divisional of U.S. patent application Ser. No. 09/949,026, filed Sep. 7, 2001, now U.S. Pat. No. 6,590,105 which claimed priority from U.S. Provisional Application Ser. No. 60/231,623, filed Sep. 11, 2000, both of which are hereby incorporated by reference in their entirety.

FIELD OF THE INVENTION

The present invention relates to certain resorcinol derivatives and their use as skin lightening agents.

BACKGROUND OF THE INVENTION

The terms "lightening agent" and "depigmentation agent" are used interchangeably throughout this document.

Skin color in humans arises from a complex series of cellular processes that are carried out within a unique population of cells called melanocytes. Melanocytes are located in the lower part of the epidermis, and their function is to synthesize a pigment, melanin, which protects the body from the damaging effects of ultraviolet radiation.

When skin is exposed to ultraviolet radiation, such as that contained in sunlight, melanocytes increase their synthesis of melanin. Melanin is deposited in melanosomes, which are vesicles found within the cell. The melanosomes are extruded from the cell and carried to the surface of the skin by keratinocytes, which internalize the melanin-containing melanosomes. The end result is that the visible layers of the skin exhibit a brown color typically known as a "tan". The darkness of the color observed in the skin is proportionate to the amount of melanin synthesized by melanocytes and transferred to the keratinocytes.

The mechanism by which skin pigmentation is formed, melanogenesis, is particularly complex and schematically involves the following main steps: Tyrosine→L-Dopa→Dopaquinone→Dopachrome→Melanins. The first two reactions in this series are catalyzed by the enzyme tyrosinase. The activity of tyrosinase is promoted by the action of α-melanocyte stimulating hormone or UV rays. It is well established that a substance has a depigmenting effect if it acts directly on the vitality of the epidermal melanocytes where melanogenesis normally occurs and/or if it interferes with one of the stages in melanin biosynthesis. The active compounds that are employed in the various methods and compositions of this invention inhibit tyrosinase and thus inhibit or decrease melanin biosynthesis.

There is a strong demand for agents that enable acquired deposition sites, such as spots or freckles, to be restored to a normal skin color. For this purpose, a variety of agents and methods have been developed and put on the market. Examples of such methods are (a) a method wherein vitamin C (L-ascorbic acid) having good reducing ability is administered orally in large amounts, (b) a method wherein glutathione is administered parenterally; (c) a method wherein a peroxide, such as hydrogen peroxide, zinc peroxide, sodium peroxide and the like, is administered: and (d) a method wherein vitamin C or cysteine is administered topically in the form of an ointment, cream, lotion or the like. Vitamin C has a problem with respect to stability and becomes so unstable in water-containing systems that they will cause changes in odor and color. Thiol compounds such as glutathione and cysteine do not exhibit a satisfactory depigmental effect since the development of the effect is very slow.

The substances in widest use at the present time as depigmentors are, in particular, hydroquinone and its derivatives, particularly its ethers such as hydroquinone monomethyl ether. These compounds, while effective, are known to produce side effects that can be dangerous. Hydroquinone, use of which is limited to a concentration of 2%, is both irritating and cytotoxic to the melanocyte.

U.S. Pat. No. 4,526,179 refers to certain hydroquinone fatty esters that have good activity and are less irritating and more stable than hydroquinone.

Japanese Patent Application No. 27909/86 refers to other hydroquinone derivatives that do not have the drawbacks of hydroquinone but that have relatively poor efficacy.

U.S. Pat. No. 5,449,518 refers to 2,5-dihydoxyphenyl carboxylic acid derivatives as skin depigmentation agents.

European Patent Application EP 341,664A1 refers to certain resorcinol derivatives as tyrosinase inhibitors and skin depigmentation agents.

PCT International Publication WO 99/15148 refers to certain resorcinol derivatives as tyrosinase inhibitors and skin depigmentation agents.

The use of topical depigmention agents that have good efficacy and are harmless is particularly desirable for treating the following: regional hyperpigmentation caused by melanocytic hyperactivity, such as idiopathic melasma occurring either during pregnancy (mask of pregnancy or chloasma) or secondary to estrogen-progesterone contraception; local hyperpigmentation caused by benign melanocytic hyperactivity and proliferation such as lentigo senilis or liver spots; accidental hyperpigmentation such as post-lesional photosensitization and scarring; and certain forms of leukoderma such as vitiligo where, if the injured skin cannot be repigmented, the residual zones of normal skin are depigmented to impart a homogeneous white color to the entire skin.

SUMMARY OF INVENTION

The resorcinol derivatives of formula I, which are defined below and used in the various methods and compositions of this invention, are useful in the treatment of the foregoing dermatological conditions as well as other dermatological conditions, some of which are referred to later in this document, for which the subject being treated desires, for medicinal or cosmetic purposes, to lighten or reduce the pigmentation of the skin affected by the condition.

The resorcinol derivatives of formula I are also useful for the treatment of inflammatory disorders such as psoriasis, dermatitis and acne, and for the treatment of dandruff.

The invention thus provides a compound of formula I:

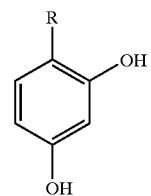

or a pharmaceutically acceptable salt thereof, wherein:

R is a $(C_3-C_8)$cycloalkyl ring or $(C_5-C_8)$cycloalkenyl ring, wherein either the cycloalkyl ring or cycloalkenyl ring is substituted by one of —N(R$^1$)SO$_2$(CHR$^1$)$_n$R$^2$ or —(C$_1$–C$_6$)alkylN(R$^1$)SO$_2$(CHR$^1$)$_n$R$^2$, wherein each R$^1$ is independently selected from hydrogen, $(C_1-C_6)$alkyl, phenyl and benzyl; R$^2$ is aryl, heteroaryl or heterocycloalkyl optionally substituted with one or more substituents independently selected from halogen, OH, —($C_1$–$C_6$)alkyl, —($C_1$–$C_6$)alkoxy, trifluoromethoxy, —S(O)$_m$($C_1$–$C_6$)alkyl, amino, —N($R^1$)CO($C_1$–$C_6$)alkyl, COO$R^1$, —($C_1$–$C_6$)alkylCOO$R^1$, —CO($C_1$–$C_6$)alkyl, —($C_1$–$C_6$)alkylOH, —($C_1$–$C_6$)alkylamino, di-(($C_1$–$C_6$)alkyl)amino, nitro, cyano, —CONH(CHR$^1$)$_n$CO$_2$R$^1$, —CONR$^1$N(R$^1$)$_2$, trifluoromethyl, aryl, heteroaryl, and heterocycloalkyl; n is an integer from 0 to 6; and m is an integer from 0 to 2;

with the proviso that the cycloalkenyl ring is not aromatic.

Where R is a cyclohexyl or cyclohexenyl ring, the ring is preferably substituted at the 3- or 4-position, and more preferably at the 4-position.

Where R is a cyclopentyl or cyclopentenyl ring, the ring is preferably substituted at the 3-position.

In a preferred embodiment, R is substituted by one of —($C_1$–$C_6$)alkylN($R^1$)SO$_2$(CHR$^1$)$_n$R$^2$.

In a further preferred embodiment, R is substituted by one of —N($R^1$)SO$_2$(CHR$^1$)$_n$R$^2$.

In a preferred embodiment, $R^1$ is H.
In a preferred embodiment, n is 0.
In a preferred embodiment, n is 1.
In a preferred embodiment, n is 2.
In a preferred embodiment, m is 2.
In a preferred embodiment, $R^1$ is H; and n is 0.
In a preferred embodiment, $R^1$ is H; n is 0; and m is 2.

The invention further provides a compound selected from the group consisting of:

N-[cis-4-(2,4-Dihydroxyphenyl)cyclohexyl]benzenesulfonamide;
4-Chloro-N-[cis-4-(2,4-dihydroxyphenyl)cyclohexyl]benzenesulfonamide;
3-Chloro-N-[cis-4-(2,4-dihydroxyphenyl)cyclohexyl]-4-fluorobenzenesulfonamide;
N-[cis-4-(2,4-Dihydroxyphenyl)cyclohexyl]-2-thiophenesulfonamide;
5-Chloro-N-[cis-4-(2,4-dihydroxyphenyl)cyclohexyl]-2-thiophenesulfonamide;
N-[cis-4-(2,4-Dihydroxyphenyl)cyclohexyl]-3-nitrobenzenesulfonamide;
N-[cis-4-(2,4-Dihydroxyphenyl)cyclohexyl]-4-nitrobenzenesulfonamide;
N-[cis-4-(2,4-Dihydroxyphenyl)cyclohexyl]-2,4-dinitrobenzenesulfonamide;
3-Cyano-N-[cis-4-(2,4-dihydroxyphenyl)cyclohexyl]benzenesulfonamide;
N-[cis-4-(2,4-Dihydroxyphenyl)cyclohexyl]-4-(methylsulfonyl)benzenesulfonamide;
N-[trans-4-(2,4-Dihydroxyphenyl)cyclohexyl]benzenesulfonamide;
N-[cis-4-(2,4-Dihydroxyphenyl)cyclohexyl]-2-naphthalenesulfonamide;
N-[cis-4-(2,4-Dihydroxyphenyl)cyclohexyl]-4-methylbenzenesulfonamide;
N-[trans-4-(2,4-Dihydroxyphenyl)cyclohexyl]-4-methylbenzenesulfonamide;
N-[cis-4-(2,4-Dihydroxyphenyl)cyclohexyl]-4-methoxybenzenesulfonamide;
N-[cis-4-(2,4-Dihydroxyphenyl)cyclohexyl]-5-(dimethylamino)-1-naphthalenesulfonamide;
N-[cis-4-(2,4-Dihydroxyphenyl)cyclohexyl]-1-methyl-1H-imidazole-4-sulfonamide;
N-[cis-4-(2,4-Dihydroxyphenyl)cyclohexyl]-5-(3-isoxazolyl)-2-thiophenesulfonamide;
Methyl 3-({[cis-4-(2,4-dihydroxyphenyl)cyclohexyl]amino}sulfonyl)benzoate;
Methyl 4-({[cis-4-(2,4-dihydroxyphenyl)cyclohexyl]amino}sulfonyl)benzoate;
Methyl 3-({[trans-4-(2,4-dihydroxyphenyl)cyclohexyl]amino}sulfonyl)benzoate;
Methyl 4-({[trans-4-(2,4-dihydroxyphenyl)cyclohexyl]amino}sulfonyl)benzoate;
4-Cyano-N-[trans-4-(2,4-dihydroxyphenyl)cyclohexyl]benzenesulfonamide;
N-[2-Chloro-4-({[cis-4-(2,4-dihydroxyphenyl)cyclohexyl]amino}sulfonyl)phenyl]acetamide;
4-Amino-3-chloro-N-[cis-4-(2,4-dihydroxyphenyl)cyclohexyl]benzenesulfonamide;
4-Acetyl-N-[cis-4-(2,4-dihydroxyphenyl)cyclohexyl]benzenesulfonamide;
N-[cis-4-(2,4-Dihydroxyphenyl)cyclohexyl]-4-(trifluoromethoxy)benzenesulfonamide;
N-[trans-4-(2,4-Dihydroxyphenyl)cyclohexyl]-4-fluorobenzenesulfonamide;
N-[trans-4-(2,4-Dihydroxyphenyl)cyclohexyl]-2,4-difluorobenzenesulfonamide;
N-[trans-4-(2,4-Dihydroxyphenyl)cyclohexyl]-2,3,4,5,6-pentafluorobenzene sulfonamide;
N-[trans-4-(2,4-Dihydroxyphenyl)cyclohexyl]-3-(trifluoromethyl)benzenesulfonamide;
N-[trans-4-(2,4-Dihydroxyphenyl )cyclohexyl]-3,5-bis(trifluoromethyl)benzene sulfonamide;
N-[cis-4-(2,4-Dihydroxyphenyl)cyclohexyl](phenyl)methanesulfonamide;
2-Chloro-N-[cis-4-(2,4-dihydroxyphenyl )cyclohexyl]-5-(trifluoromethyl)benzene sulfonamide;
3,5-Dichloro-N-[cis-4-(2,4-dihydroxyphenyl )cyclohexyl]benzenesulfonamide;
4-Bromo-N-[cis-4-(2,4-dihydroxyphenyl)cyclohexyl]-2,5-difluorobenzenesulfonamide;
N-[cis-4-(2,4-Dihydroxyphenyl)cyclohexyl]-3,5-bis(trifluoromethyl)benzene sulfonamide;
N-[cis-4-(2,4-Dihydroxyphenyl)cyclohexyl]-1-naphthalenesulfonamide;
N-[cis-4-(2,4-Dihydroxyphenyl)cyclohexyl]-3-(hydroxymethyl) benzenesulfonamide;
N-[cis-4-(2,4-Dihydroxyphenyl)cyclohexyl]-4-(hydroxymethyl)benzene sulfonamide;
4-({[cis-4-(2,4-Dihydroxyphenyl)cyclohexyl]amino}sulfonyl)benzoic acid;
3-({[cis-4-(2,4-Dihydroxyphenyl)cyclohexyl]amino}sulfonyl)benzoic acid;
4-({[trans-4-(2,4-Dihydroxyphenyl)cyclohexyl]amino}sulfonyl)benzoic acid;
3-({[trans-4-(2,4-Dihydroxyphenyl)cyclohexyl]amino}sulfonyl)benzoic acid;
Benzyl (2S)-2-{[3-({[cis-4-(2,4-dihydroxyphenyl)cyclohexyl]amino}sulfonyl) benzoyl]amino}-3-phenylpropanoate;
(2S)-2-({[3-({[cis-4-(2,4-Dihydroxyphenyl)cyclohexyl]amino}sulfonyl)benzoyl]amino}-3-phenylpropanoic acid;
Benzyl 3-{[3-({[cis-4-(2,4-dihydroxyphenyl)cyclohexyl]amino}sulfonyl)benzoyl]amino}propanoate;
N-[3-({[cis-4-(2,4-Dihydroxyphenyl)cyclohexyl]amino}sulfonyl)benzoyl]-β-alanine;
N-[cis-4-(2,4-Dihydroxyphenyl)cyclohexyl]-4-hydrazinocarbonyl)benzenesulfonamide;
N-[cis-4-(2,4-Dihydroxyphenyl)cyclohexyl]-3-(1H-tetrazol-5-yl)benzenesulfonamide; and a pharmaceutically acceptable salt thereof.

The present invention further provides a pharmaceutical composition for lightening skin or reducing the pigmentation of skin in a human, comprising a pharmaceutically acceptable carrier, and a skin-lightening or pigmentation-reducing effective amount of a compound of formula I:

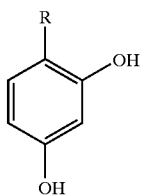

or a pharmaceutically acceptable salt thereof, wherein:

R is a $(C_3-C_8)$cycloalkyl ring or $(C_5-C_8)$cycloalkenyl ring, wherein either the cycloalkyl ring or cycloalkenyl ring is substituted by one of $-N(R^1)SO_2(CHR^1)_nR^2$ or $-(C_1-C_6)alkylN(R^1)SO_2(CHR^1)_nR^2$, wherein each $R^1$ is independently selected from hydrogen, $(C_1-C_6)$alkyl, phenyl and benzyl; $R^2$ is aryl, heteroaryl or heterocycloalkyl optionally substituted with one or more substituents independently selected from halogen, OH, $-(C_1-C_6)$alkyl, $-(C_1-C_6)$alkoxy, trifluoromethoxy, $-S(O)_m(C_1-C_6)$alkyl, amino, $-N(R^1)CO(C_1-C_6)$alkyl, $COOR^1$, $-(C_1-C_6)$alkylCOOR$^1$, $-CO(C_1-C_6)$alkyl, $-(C_1-C_6)$alkylOH, $-(C_1-C_6)$alkylamino, di-$((C_1-C_6)$alkyl)amino, nitro, cyano, $-CONH(CHR^1)_nCO_2R^1$, $-CONR^1N(R^1)_2$, trifluoromethyl, aryl, heteroaryl, and heterocycloalkyl; n is an integer from 0 to 6; and m is an integer from 0 to 2;

with the proviso that the cycloalkenyl ring is not aromatic.

Where R is a cyclohexyl or cyclohexenyl ring, the ring is preferably substituted at the 3- or 4-position, and more preferably at the 4-position.

Where R is a cyclopentyl or cyclopentenyl ring, the ring is preferably substituted at the 3-position.

In a preferred embodiment, R is substituted by one of $-(C_1-C_6)alkylN(R^1)SO_2(CHR^1)_nR^2$.

In a further preferred embodiment, R is substituted by one of $-N(R^1)SO_2(CHR^1)_nR^2$.

In a preferred embodiment, $R^1$ is H.
In a preferred embodiment, n is 0.
In a preferred embodiment, n is 1.
In a preferred embodiment, n is 2.
In a preferred embodiment, m is 2.
In a preferred embodiment, $R^1$ is H; and n is 0.
In a preferred embodiment, $R^1$ is H; n is 0; and m is 2.

In a preferred embodiment, the pharmaceutical composition of the present invention is adapted for topical application.

The invention further provides a pharmaceutical composition comprising a pharmaceutically acceptable carrier and a skin-lightening or pigmentation-reducing effective amount of a compound selected from the group consisting of:

N-[cis-4-(2,4-Dihydroxyphenyl)cyclohexyl] benzenesulfonamide;
4-Chloro-N-[cis-4-(2,4-dihydroxyphenyl)cyclohexyl] benzenesulfonamide;
3-Chloro-N-[cis-4-(2,4-dihydroxyphenyl)cyclohexyl]-4-fluorobenzenesulfonamide;
N-[cis-4-(2,4-Dihydroxyphenyl )cyclohexyl]-2-thiophenesulfonamide;
5-Chloro-N-[cis-4-(2,4-dihydroxyphenyl)cyclohexyl]-2-thiophenesulfonamide;
N-[cis-4-(2,4-Dihydroxyphenyl )cyclohexyl]-3-nitrobenzenesulfonamide;
N-[cis-4-(2,4-Dihydroxyphenyl)cyclohexyl]-4-nitrobenzenesulfonamide;
N-[cis-4-(2,4-Dihydroxyphenylcyclohexyl]-2,4-dinitrobenzenesulfonamide;
3-Cyano-N-[cis-4-(2,4-dihydroxyphenyl)cyclohexyl] benzenesulfonamide;
N-[cis-4-(2,4-Dihydroxyphenyl)cyclohexyl]-4-(methylsulfonyl)benzenesulfonamide;
N-[trans-4-(2,4-Dihydroxyphenyl)cyclohexyl] benzenesulfonamide;
N-[cis-4-(2,4-Dihydroxyphenyl)cyclohexyl]-2-naphthalenesulfonamide;
N-[cis-4-(2,4-Dihydroxyphenyl)cyclohexyl]-4-methylbenzenesulfonamide;
N-[trans-4-(2,4-Dihydroxyphenyl )cyclohexyl]-4-methylbenzenesulfonamide;
N-[cis-4-(2,4-Dihydroxyphenyl)cyclohexyl]-4-methoxybenzenesulfonamide;
N-[cis-4-(2,4-Dihydroxyphenyl)cyclohexyl]-5-(dimethylamino)-1-naphthalenesulfonamide;
N-[cis-4-(2,4-Dihydroxyphenyl)cyclohexyl]-1-methyl-1H-imidazole-4-sulfonamide;
N-[cis-4-(2,4-Dihydroxyphenyl)cyclohexyl]-5-(3-isoxazolyl)-2-thiophenesulfonamide;
Methyl 3-({[cis-4-(2,4-dihydroxyphenyl)cyclohexyl] amino}sulfonyl)benzoate;
Methyl 4-({[cis-4-(2,4-dihydroxyphenyl)cyclohexyl] amino}sulfonyl)benzoate;
Methyl 3-({[trans-4-(2,4-dihydroxyphenyl)cyclohexyl] amino}sulfonyl)benzoate;
Methyl 4-({[trans-4-(2,4-dihydroxyphenyl)cyclohexyl] amino}sulfonyl)benzoate;
4-Cyano-N-[trans-4-(2,4-dihydroxyphenyl)cyclohexyl] benzenesulfonamide;
N-[2-Chloro-4-({[cis-4-(2,4-dihydroxyphenyl)cyclohexyl] amino}sulfonyl)phenyl]acetamide;
4-Amino-3-chloro-N-[cis-4-(2,4-dihydroxyphenyl) cyclohexyl]benzenesulfonamide;
4-Acetyl-N-[cis-4-(2,4-dihydroxyphenyl)cyclohexyl] benzenesulfonamide;
N-[cis-4-(2,4-Dihydroxyphenyl)cyclohexyl]-4-(trifluoromethoxy)benzenesulfonamide;
N-[trans-4-(2,4-Dihydroxyphenyl)cyclohexyl]-4-fluorobenzenesulfonamide;
N-[trans-4-(2,4-Dihydroxyphenyl)cyclohexyl]-2,4-difluorobenzenesulfonamide;
N-[trans-4-(2,4-Dihydroxyphenyl)cyclohexyl]-2,3,4,5,6-pentafluorobenzene sulfonamide;
N-[trans-4-(2,4-Dihydroxyphenyl)cyclohexyl]-3-(trifluoromethyl)benzenesulfonamide;
N-[trans-4-(2,4-Dihydroxyphenyl)cyclohexyl]-3,5-bis (trifluoromethyl)benzene sulfonamide;
N-[cis-4-(2,4-Dihydroxyphenyl)cyclohexyl](phenyl) methanesulfonamide;
2-Chloro-N-[cis-4-(2,4-dihydroxyphenyl)cyclohexyl]-5-(trifluoromethyl)benzene sulfonamide;
3,5-Dichloro-N-[cis-4-(2,4-dihydroxyphenyl)cyclohexyl] benzenesulfonamide;
4-Bromo-N-[cis-4-(2,4-dihydroxyphenyl)cyclohexyl]-2,5-difluorobenzenesulfonamide;
N-[cis-4-(2,4-Dihydroxyphenyl)cyclohexyl]-3,5-bis (trifluoromethyl)benzene sulfonamide;
N-[cis-4-(2,4-Dihydroxyphenyl)cyclohexyl]-1-naphthalenesulfonamide;
N-[cis-4-(2,4-Dihydroxyphenyl)cyclohexyl]-3-(hydroxymethyl) benzenesulfonamide;
N-[cis-4-(2,4-Dihydroxyphenyl )cyclohexyl]-4-(hydroxymethyl)benzene sulfonamide;
4-({[cis-4-(2,4-Dihydroxyphenyl)cyclohexyl] amino}sulfonyl)benzoic acid;
3-({[cis-4-(2,4-Dihydroxyphenyl)cyclohexyl] amino}sulfonyl)benzoic acid;

4-({[trans-4-(2,4-Dihydroxyphenyl)cyclohexyl]
amino}sulfonyl)benzoic acid;
3-({[trans-4-(2,4-Dihydroxyphenyl)cyclohexyl]
amino}sulfonyl )benzoic acid;
Benzyl (2S)-2-{[3-({[cis-4-(2,4-dihydroxyphenyl)
cyclohexyl]amino}sulfonyl) benzoyl]amino}-3-
phenylpropanoate;
(2S)-2-{[3-({[cis-4-(2,4-Dihydroxyphenyl)cyclohexyl]
amino}sulfonyl)benzoyl]amino}-3-phenylpropanoic
acid;
Benzyl 3-{[3-({[cis-4-(2,4-dihydroxyphenyl)cyclohexyl]
amino}sulfonyl)benzoyl]amino}propanoate;
N-[3-({[cis-4-(2,4-Dihydroxyphenyl)cyclohexyl]
amino}sulfonyl)benzoyl]-β-alanine;
N-[cis-4-(2,4-Dihydroxyphenyl)cyclohexyl]-4-
hydrazinocarbonyl)benzenesulfonamide;
N-[cis-4-(2,4-Dihydroxyphenyl)cyclohexyl]-3-(1H-
tetrazol-5-yl)benzenesulfonamide; and a pharmaceutically acceptable salt thereof.

The invention further provides a cosmetic composition comprising a topical carrier in combination with any one or more of the compounds of formula I, or a pharmaceutically acceptable salt thereof.

The present invention further provides a method of lightening skin in a human, comprising administering to said human a skin-lightening or pigmentation-reducing effective amount of a compound of formula I or a pharmaceutically acceptable salt thereof. In a preferred embodiment, the present invention provides a method of lightening skin in a human in need of said treatment, comprising administering to said human a skin-lightening effective amount of a compound of formula I or a pharmaceutically acceptable salt thereof.

The present invention further provides a method of inhibiting tyrosinase in a human, comprising administering to said human a tyrosinase-inhibiting effective amount of a compound of formula I, or a pharmaceutically acceptable salt thereof. In a preferred embodiment, the present invention provides a method of inhibiting tyrosinase in a human in need of said treatment, comprising administering to said human a tyrosinase-inhibiting effective amount of a compound of formula I or a pharmaceutically acceptable salt thereof.

The present invention further provides a topical or transdermal pharmaceutical composition for the treatment of an inflammatory disorder or condition such as psoriasis. dermatitis or acne, or for the treatment of dandruff, in a human in need of said treatment, comprising a pharmaceutically acceptable carrier, and an amount of a compound of formula I, or a pharmaceutically acceptable salt thereof, which amount is effective in treating such disorder or condition.

The present invention further provides a method of treating an inflammatory disorder, such as psoriasis, dermatitis or acne, or a method of treating dandruff, in a human in need of said treatment, comprising administering to said human an amount of a compound of formula I or a pharmaceutically acceptable salt thereof, which amount is effective in treating such disorder or condition.

The present invention further provides a kit, comprising a container comprising one or more specific compounds or pharmaceutically acceptable salts thereof, or pharmaceutical compositions, of the present invention that lighten skin. The kit may further comprise printed instructions as a label or package insert directing the use of the enclosed compound or composition to lighten skin pigmentation.

As used herein, the terms "treat" and "treating", and the like, refer to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "alkyl", as used herein, unless otherwise indicated, includes saturated monovalent hydrocarbon radicals having straight, branched or cyclic moieties or combinations thereof. Any substituents or functional groups on the alkyl group, as indicated herein, can be substituted anywhere on the alkyl group.

The term "aryl", as used herein, refers to phenyl or naphthyl. The aryl group can be optionally substituted with one or more substituents, preferably from one to two substituents, independently selected from halogen, OH, —$(C_1-C_6)$alkyl, —$(C_1-C_6)$alkoxy, trifluoromethoxy, —$S(O)_m(C_1-C_6)$alkyl, amino, —$N(R^1)CO(C_1-C_6)$alkyl, $COOR^1$, —$(C_1-C_6))$alkyl$COOR^1$, —$CO(C_1-C_6)$alkyl, —$(C_1-C_6)$alkylOH, —$(C_1-C_6)$alkylamino, di-$((C_1-C_6)$alkyl)amino, nitro, cyano, —$CONH(CHR^1)_nCO_2R^1$, —$CONR^1N(R^1)_2$, and trifluoromethyl. Any substituents or functional groups on the aryl group, as indicated herein, can be substituted anywhere on the aryl group.

The term "one or more substituents", as used herein, refers to a number of substituents that equals from one to the maximum number of substituents possible based on the number of available bonding sites.

The term "halo", as used herein, refers to halogen and, unless otherwise indicated, includes chloro, fluoro, bromo and iodo.

The term "heteroaryl", as used herein, refers to $(C_2-C_9)$ heteroaryl, and preferably a 5- or 6-membered heteroaryl, containing one to five N, O or S atoms. In a preferred embodiment, the heteroaryl is selected from furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidinyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyridinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolinyl, quinolinyl, phthalazinyl, quinoxalinyl, quinazolinyl, and benzoxazinyl. One of ordinary skill in the art will understand that the connection of said $(C_2-C_9)$heteroaryl ring can be through a carbon atom or through a nitrogen heteroatom where possible.

In a preferred embodiment, the heteroaryl group is optionally substituted with one or more substituents, preferably from one to two substituents, independently selected from halogen, OH, —$(C_1-C_6)$alkyl, —$(C_1-C_6)$alkoxy, trifluoromethoxy, —$S(O)_m(C_1-C_6)$alkyl, amino, —$N(R^1)$ $CO(C_1-C_6)$alkyl, $COOR^1$, —$(C_1-C_6)$alkyl$COOR^1$, —$CO$ $(C_1-C_6)$alkyl, —$(C_1-C_6)$alkylOH, 13 $(C_1-C_6)$alkylamino, di-$((C_1-C_6)$alkyl)amino, nitro, cyano, —CONH $(CHR^1)_nCO_2R^1$, —$CONR^1N(R^1)_2$, and trifluoromethyl. Any substituents or functional groups on the heteroaryl group, as indicated herein, can be substituted anywhere on the heteroaryl group.

The term "heterocycloalkyl", as used herein, refers to a $(C_2-C_9)$heterocycloalkyl, and preferably a 5- or 6-membered heterocycloalkyl, containing one to five N, O or S atoms. In a preferred embodiment, the heterocycloalkyl group is selected from pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, and chromanyl. One of ordinary skill in the art will understand that the connection of said heterocycloalkyl ring can be through a carbon atom or through a nitrogen heteroatom where possible.

In a preferred embodiment, the heterocycloalkyl group is optionally substituted with one or more substituents, preferably from one to two substituents, independently selected from halogen, OH, —($C_1$-$C_6$)alkyl, —($C_1$-$C_6$)alkoxy, trifluoromethoxy, —S(O)$_m$($C_1$-$C_6$)alkyl, amino, —N($R^1$)CO($C_1$-$C_6$)alkyl, COOR$^1$, —($C_1$-$C_6$)alkylCOOR$^1$, —CO($C_1$-$C_6$)alkyl, —($C_1$-$C_6$)alkylOH, —($C_1$-$C_6$)alkylamino, di-(($C_1$-$C_6$)alkyl)amino, nitro, cyano, —CONH(CHR$^1$)$_n$CO$_2$R$^1$, —CONR$^1$N(R$^1$)$_2$, and trifluoromethyl. Any substituents or functional groups on the heterocycloalkyl group, as indicated herein, can be substituted anywhere on the aryl group.

Compounds of formula I may contain chiral centers and therefore may exist in different enantiomeric and diastereomeric forms. This invention relates to all optical isomers, stereoisomers and tautomers of the compounds of formula I, and mixtures thereof, and to all pharmaceutical compositions and methods of treatment defined above that contain or employ them, respectively.

Formula I, as defined above, also includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

The present invention also relates to the pharmaceutically acceptable acid addition and base salts of any of the aforementioned compounds of formula I. The acids that are used to prepare the pharmaceutically acceptable acid addition salts of the aforementioned base compounds of this invention are those that form non-toxic acid addition salts, i.e., salts containing pharmacologically acceptable anions, such as the hydrochloride, hydrobromide, hydroiodide, nitrate, sulfate, bisulfate, phosphate, acetate, lactate, citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

As used herein, a "skin-lightening or pigmentation reducing amount of a compound of formula I", and the like, means an amount or concentration of the compound capable of detectably lightening skin or reducing pigmentation in a human, as determined by any standard assay. The active compound is typically administered in a pharmaceutical composition and for a standard course of treatment that produces the desired result of skin depigmentation.

As used herein, a "tyrosinase-inhibiting effective amount of a compound of formula I", and the like, means an amount or concentration of the compound capable of detectably inhibiting tyrosinase activity in a human, as determined by any standard assay, such as those described below.

As used herein, an "amount of a compound of formula I capable of treating an inflammatory disorder such as psoriasis, dermatitis or acne, or treating dandruff", and the like, means an amount or concentration of the compound capable of detectably ameliorating, reducing, eliminating, slowing, or preventing the progression of, any symptom or condition associated with or caused by such disorder or condition, in a human, as determined by any standard assay.

DETAILED DESCRIPTION OF THE INVENTION

The compounds of formula I may be prepared as described in the following reaction schemes and discussion. Unless otherwise indicated, R$^1$ and structural formula I in the reaction schemes and discussion that follow are as defined above.

Scheme 1

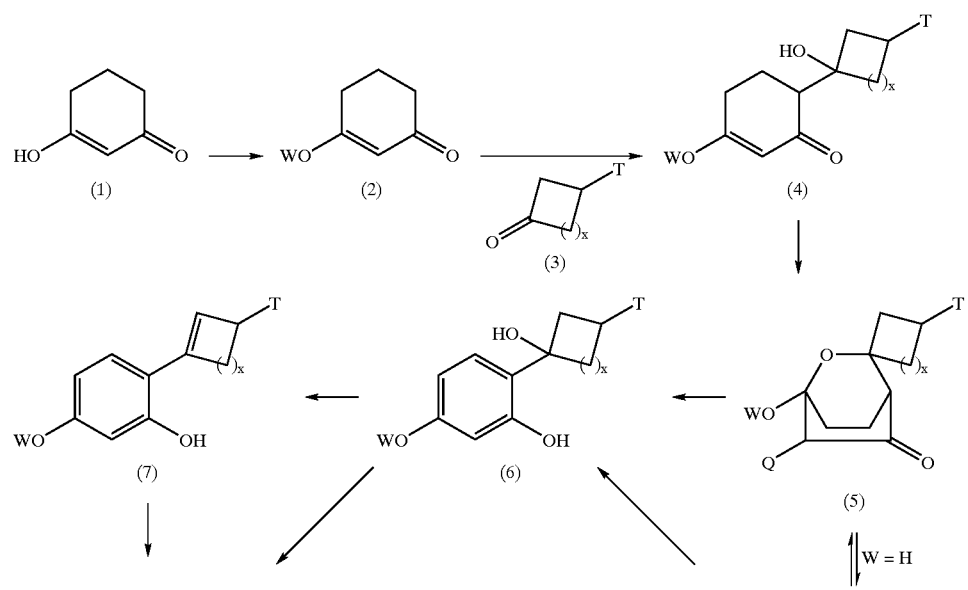

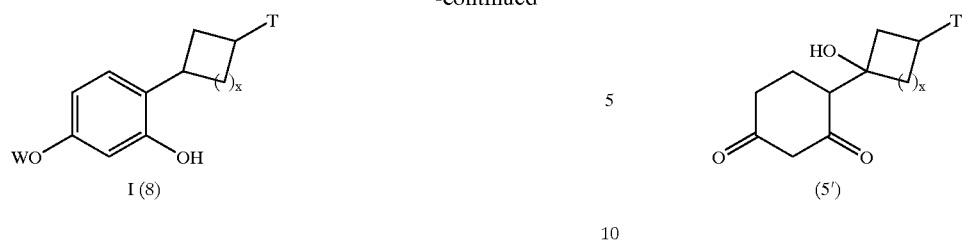
Scheme 2
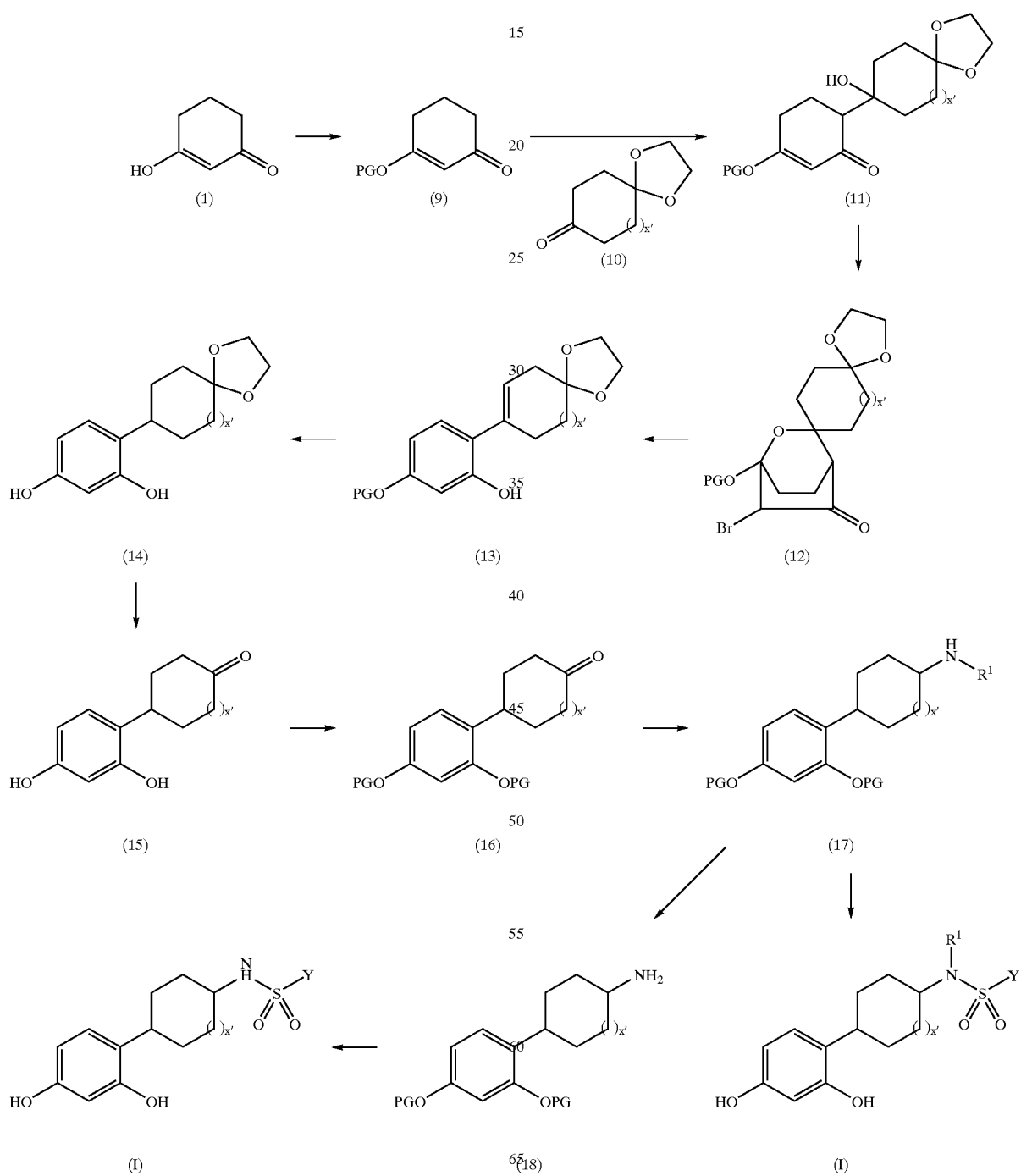

Referring to Scheme 1, where x is zero to five, compounds of formula (2) can be prepared starting with compound (1), which is commercially available (Aldrich Chemical Co.). A suitable protecting group can be selected as will be evident to those of skill in the art and conversion to compounds of formula (2) can occur under standard conditions. One example of a suitable protecting group is benzyl, and condensation can occur between compound (1) and benzyl alcohol with the removal of water using Dean-Stark apparatus to give compounds of formula (2). Compounds of formula (3), where T is a sulfonamide moiety have been previously reported (Fonken, G. S. et al. *J. Org. Chem.*, 1968, 33, 3182 and Dubuffet, T. et al. *Synth. Commun.*, 1997, 27, 1123). Alternatively, T is a functional group that may be converted to a sulfonamide using standard chemistry that will be obvious to those with skill in the art. Condensation of compounds of formula (2) with compounds of formula (3) may occur using standard techniques, for instance, treatment of compounds of formula (2) with a base, such as lithium diisopropylamide or lithium hexamethyldisilazide, in an ethereal solvent followed by the addition of a compound of formula (3) would give compounds of formula (4). When W is hydrogen (H), as opposed to a protecting group (PG), condensation of compounds of formula (2) with compounds of formula (3) requires the use of at least two equivalents of a suitable base such as lithium diisopropylamide in a suitable solvent such as tetrahydrofuran, with a suitable co-solvent such as hexamethylphosphoramide. Treatment of compounds of formula (4) with a suitable halogenating reagent such as, for example, N-bromosuccinimide in a chlorinated solvent, such as dichloromethane or chloroform, at about room temperature, can give compounds of formula (5) where Q is halo, and preferably bromo. Where W is H, the compound of formula (5) may exist in equilibrium with the compound of formula (5').

Compounds of formula (6) may be generated from compounds of formula (5) or (5') under suitable conditions. Such conditions may involve treating compounds of formula (5) or (5') with a base such as, e.g., 1,8-diazobicyclo[5.4.0] undec-7-ene in a suitable solvent such as N,N-dimethylformamide at about room temperature. Where T represents a sulfonamide moiety, compounds of formula (7) may be generated from compounds of formula (5), (5') or (6) under suitable reaction conditions. Such conditions may involve treating compounds of formula (5) or (5') or (6) with a base such as, e.g., 1,8-diazobicyclo[5.4.0]undec-7-ene in a suitable solvent such as N,N-dimethylformamide at about 140° C. Other solvents such as toluene or N-methylpyrrolidinone may also be useful for this purpose. Where T represents a sulfonamide moiety, compounds of formula (8) may be generated from compounds of formula (6) using standard techniques, e.g., treating compounds of formula (6) with triethylsilane in the presence of a Lewis acid such as boron trifluoride in a chlorinated solvent. Hydrogenation of compounds of formula (7) under standard conditions, e.g., hydrogen gas and palladium on charcoal in ethanol, also yields compounds of formula (8). Where W is a protecting group, compounds of formula (I) can be formed by treating compounds of formula (7) or (8) under standard conditions that will be obvious to those with skill in the art. Where T is not a sulfonamide group, compounds of formula (7) and (8) may be converted into compounds of formula (I) using standard chemistry that will be obvious to those with skill in the art.

Referring to Scheme 2, as an example of a more specific scheme where x' is zero or one, compounds of formula (9) can be prepared starting with compound (1). Conversion to compounds of formula (9) can occur under standard conditions, for instance where the protecting group is benzyl, condensation can occur between compound (1) and benzyl alcohol with the removal of water using Dean-Stark apparatus. Condensation of compounds of formula (9) with compounds of formula (10) may occur using standard techniques, for instance, treatment of compounds of formula (9) with a base such as lithium diisopropylamide in an ethereal solvent followed by the addition of a compound of formula (10) (where x'=1, compound (10) is commercially available from Aldrich Chemical Co.) would give compounds of formula (11). Treatment of compounds of formula (11) with a suitable brominating reagent, such as N-bromosuccinimide, in a chlorinated solvent at about room temperature, can give compounds of formula (12). Compounds of formula (13) may then be generated from compounds of formula (12) under suitable reaction conditions. Such conditions may involve treating compounds of formula (12) with a base such as 1,8-diazobicyclo[5.4.0]undec-7-ene in a suitable solvent such as N,N-dimethylformamide at about 140° C. Subjection of compounds of formula (13) to standard hydrogenation conditions, e.g., hydrogen gas and palladium on charcoal in an ethanol/tetrahydrofuran mixture, yields compounds of the general formula (14) when the protecting group was benzyl. Compounds of formula (15) may then be obtained by subjecting compounds of formula (14) to acidic conditions.

Protection of compounds of formula (15) with a suitable protecting group such as tert-butyldimethylsilyl can occur under standard conditions, e.g., compounds of formula (15) can be treated with tert-butyldimethylsilyl chloride and a suitable base such as imidazole, in a suitable solvent such as dimethylformamide at about room temperature. Treatment of compounds of formula (16) with an amine under reductive amination conditions, e.g., where $R^1$=benzyl, using benzylamine and sodium triacetoxyborohydride in a suitable solvent (dichloroethane) can give compounds of formula (17). Alternatively, compounds of formula (17) can be formed by treating compounds of formula (16) with an amine, such as benzylamine, under dehydrating conditions followed by reaction with a reducing agent such as sodium borohydride. Where $R^1$=benzyl, conversion of compounds of formula (17) to compounds of formula (18) can occur using hydrogenolysis under standard conditions, e.g., palladium on charcoal, hydrogen gas, in a suitable solvent, e.g. ethanol. Synthesis of compounds of formula I, where Y is —$(CHR^1)_nR^2$, can be obtained using conventional methods. For example, compounds of formula (17) and (18) can react with sulfonyl chlorides in a chlorinated solvent in the presence of a base (e.g. triethylamine) at about room temperature. Subsequent functional group manipulation or derivatisation of Y can be carried out using chemistry that will be obvious to those with skill in the art, and if applicable, deprotection using suitable deprotection conditions, will provide further compounds of formula (I). An example of further functional group manipulation that may occur is when Y is substituted with a carboxylic ester. Treatment with a reducing agent such as lithium aluminium hydride in an ethereal solvent such as tetrahydrafuran would give a compound in which Y is substituted with a methyl alcohol moiety.

It will be appreciated by those of skill in the art that in the processes described above, the functional groups of intermediate compounds may need to be protected by protecting groups. The use of protecting groups is well-known in the art, and is fully described, among other places, in: *Protecting*

*Groups in Organic Chemistry*, J. W. F. McOmie, (ed.), 1973, Plenum Press; and in: *Protecting Groups in Organic Synthesis*, $2^{nd}$ edition, T. W. Greene & P. G. M. Wutz, 1991, Wiley-Interscience, which are incorporated by reference in their entirety.

The compounds of formula I that are basic in nature are capable of forming a wide variety of different salts with various inorganic and organic acids. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of formula I that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of formula I. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

Compounds of formula I and their pharmaceutically acceptable salts (hereinafter "the active compounds used in this invention") are useful in the treatment of disorders of human pigmentation, including solar and simple lentigines (including age/liver spots), melasma/chloasma and postinflammatory hyperpigmentation. The active compounds used in this invention reduce skin melanin levels by inhibiting the production of melanin, whether the latter is produced constitutively or in response to UV irradiation (such as sun exposure). Thus, the active compounds used in this invention can be used to reduce skin melanin content in non-pathological states so as to induce a lighter skin tone, as desired by the user, or to prevent melanin accumulation in skin that has been exposed to UV irradiation. Thus, the active compounds used in this invention can be used simply to lighten skin where no pathological or disease condition exists. The active compounds used in this invention can also be used for cosmetic purposes. As used herein to refer to the depigmentation aspect of the invention, the term "a human in need of said treatment" refers to a human who, for any reason, whether medical or cosmetic, desires to reduce the melanin content of their skin or to prevent the melanization of their skin on any portion of their body.

The compounds of this invention can be mixed as cosmetics, quasi-drugs (where applicable), or pharmaceutical drugs. The compounds of this invention can appropriately be mixed with other components. Examples of such components include oily components such as hydrocarbons, fats and oils such as liquid paraffin, squalene, vaseline, cetyl alcohol, isostearyl alcohol, cetyl-2-ethylhexanoate, 2-octyldodecyl alcohol, glycerin triiostearate, nut oils, and lanolin, as well as wax, silicone, surfactants, thickeners, neutralizers, antiseptics, germicides, anti-oxidants, powder components, pigments, perfumes, ultraviolet light absorbents, drugs, metallic sealant, and pH modifiers.

Occurrences in the skin or hair of noticeable but undesired pigmentation as a result of melanin production, overproduction or underproduction can be treated using the methods of the present invention. Cosmetic applications for methods of the present invention include the topical application of compositions containing one or more of the compounds of the present invention to enhance or otherwise alter the visual appearance of skin or hair. The cosmetic compositions of the present invention are also useful to provide a smoother or softer skin appearance or texture.

The active compounds used in this invention can also be used in combination with skin peeling agents (including glycolic acid or trichloroacetic acid face peels) to lighten skin tone and prevent repigmentation. The appropriate dose regimen, the amount of each dose administered, and specific intervals between doses of the active compound will depend upon the particular active compound employed, the condition of the patient being treated, and the nature and severity of the disorder or condition being treated. Preferably, the active compound is administered in an amount and at an interval that results in the desired treatment of or improvement in the disorder or condition being treated.

An active compound used in this invention can also be used in combination with sun screens (UVA or UVB blockers) to prevent repigmentation; to protect against sun or UV-induced skin darkening or to enhance their ability to reduce skin melanin and their skin bleaching action. An active compound used in this invention can also be used in combination with retinoic acid or its derivatives or any compounds that interact with retinoic acid receptors and accelerate or enhance the invention's ability to reduce skin melanin and skin bleaching action, or enhance the invention's ability to prevent the accumulation of skin melanin. An active compound used in this invention can also be used in combination with 4-hydroxyanisole. An active compound used in this invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

As one skilled in the art would know in view of this disclosure, an active compound used in the methods of the present invention may be used alone or in combination with other compounds known in the art to affect melanin synthesis, particularly other melanin synthesis inhibitors, including tyrosinase inhibitors. Such inhibitors include those currently known in the art and those to be developed in the future. Known inhibitors include various resorcinol derivatives, kojic acid derivatives, hydroquinone, melamine, and various types of plant extracts, among others. For example, any of the compounds used according to a skin-lightening method of the present invention may be used in combination with a tyrosinase inhibitor or other skin-whitening agent, including any one or more of those agents, including compounds or extracts, described in the following patent publications: U.S. Pat. No. 4,278,656 to Nagai et al, issued Jul. 14, 1981, describing the use of kojic acid and its derivatives; U.S. Pat. No. 4,369,174 to Nagai et al., issued Jan. 18, 1983, describing the use of kojic acid and its derivatives; U.S. Pat. No. 4,959,393 to Torihara et al., issued Sep. 25, 1990, describing the use of 4-n-butylresorcinol, 4-isoamyl resorcinol and other resorcinol derivatives; U.S. Pat. No. 5,580,549 to Fukuda et al., issued Dec. 3, 1996, describing the use of various hydroxybenzoic acid derivatives; U.S. Pat. No. 6,123,959 to Jones et al., issued Sep. 26, 2000, describing the use of liposomes containing combinations of competitive inhibitors, such as arbutin, and non-competitive inhibitors, such as aloesin, of melanin synthesis; U.S. Pat. No. 6,132,740 to Hu, issued Oct. 17, 2000, describing the use of various resorcinol derivatives; U.S. Pat. No. 6,159,482 to Tuloup et al., issued Dec. 12, 2000, describing the use of various hydroxyphenyl oxamate derivatives; WO 99/32077 by L'Oreal, published Jul. 1, 1999, describing the use of various phenolic amides; WO 99/64025 by Fytokem Prod. Inc., published Dec. 16, 1999, describing the use of various dicotyledonous plant extracts; WO 00/56702 by Pfizer Inc., published Sep. 28, 2000 describing various resorcinol derivatives; WO 00/76473 by Shiseido Co. Ltd., published Dec. 12, 2000, describing the use of Withania plant extracts; EP 997140 by L'Oreal S A, published May 3, 2000, describing the use of combinations of mulberry and skullcap extracts with salicylic acid derivatives; JP 5221846 by Kunimasa Tomoji, published Aug. 31, 1993, describing the use of kojic acid derivatives; JP 7242687 by Shiseido Co. Ltd., published Sep. 19, 1995, describing the use of Trichoderma extracts; JP 7324023 by Itogawa H, published Dec. 12, 1995, describing the use of Pseudostellariae radix extracts; JP 8012552 by Shiseido Co. Ltd., published Jan. 16, 1996, describing the use of Amor seco extracts; JP 8012554 by Shiseido Co. Ltd., published Jan. 16, 1996, describing the use of Jabonciilo extracts; JP 8012557 by Shiseido Co. Ltd., published Jan. 16, 1996, describing the use of Huaca extracts; JP 8012560 by Shiseido Co. Ltd., published Jan. 16, 1996, describing the use of Copaiba extracts; JP 8012561 by Shiseido Co. Ltd., published Jan. 16, 1996, describing the use of Arnica extracts; JP 8134090 by Fujisawa, published May 28, 1996, describing the use of galactosyl-kojic acid derivatives; JP 8168378 by Kirinjo K K, published Jul. 2, 1996, describing the use of lees from rice wine production; JP 8277225 by Kansai Koso K K, published Oct. 22, 1996, describing the use of Autocarpus incisus extracts; JP 9002967 by Sanki Shoji K K, published Jan. 7, 1997, describing the use of Prunus domesticus extracts; JP 9295927 by Yagi Akira, published Nov. 18, 1997, describing the use of Aloe vera extracts; JP 10072330 by Kansai Kouso, published Mar. 17, 1998, describing the use of oxydesberatrol derivatives; JP 10081626 by Kamiyama K K, published Mar. 31, 1998, describing the use of 4-substituted benzoic acids; JP 10101543 by Kansai Kouso K K, published Apr. 21, 1998, describing the use of flavonoids; JP 11071231 by Maruzen Pharm., published Mar. 16, 1999, describing the use of bakuchiol; JP 11079934 by Kyodo Nyugyo, published Mar. 23, 1999, describing the use of low molecular weight thiol from sake lees; JP 11246347 by Shiseido Co. Ltd., published Sep. 14, 1999, describing the use of Achillea millefolium extracts; JP 11246344 by Shiseido Co. Ltd., published Sep. 14, 1999, describing the use of Gliricidia extracts; JP 2000-080023 by Kanebo Ltd., published Mar. 21, 2000, describing the use of metallothionine inducers; JP 2000-095663 by Kose K K, published Apr. 4, 2000, describing the use of various plant extracts; JP 2000-159681 by Hai Tai Confectionary Co. Ltd., published Jun. 13, 2000, describing the use of grape seed extract; JP-7206753 by Nikken Food KK, published Aug. 8, 1995, describing the use of dihydroxycurcumin derivatives; JP-5320025 by Kunimasa T, published Dec. 3, 1993, describing the use of kojic acid derivatives; and JP-59157009 by Yakurigaku Chuou K E, published Sep. 6, 1984, describing the use of β-thujaplicin, hydroquinone or a pyrone compound in combination with a melanin adsorbent; among others; which patent publications are incorporated herein by reference in their entireties.

This invention relates both to methods of lightening or reducing the pigmentation of skin in which an active compound used in this invention, and one or more of the other active ingredients, such as those referred to above, are administered together as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

An active compound of this invention will generally be administered in the form of a pharmaceutical composition comprising at least one compound of formula (I), together with a pharmaceutically acceptable vehicle or diluent. Alternatively, an active compound of this invention can be administered in the form of a cosmetic composition comprising at least one compound of formula (I), together with a cosmetically acceptable vehicle or diluent. Such a composition is generally formulated in a conventional manner utilizing solid or liquid vehicles or diluents as appropriate for topical administration, in the form of solutions, gels, creams, jellies, pastes, lotions, ointments, salves, aerosols and the like.

Examples of vehicles for application of the active compounds of this invention include an aqueous or water-alcohol solution, an emulsion of the oil-in-water or water-in-oil type, an emulsified gel, or a two-phase system. Preferably, the compositions according to the invention are in the form of lotions, creams, milks, gels, masks, microspheres or nanospheres, or vesicular dispersions. In the case of vesicular dispersions, the lipids of which the vesicles are made can be of the ionic or nonionic type, or a mixture thereof. Such vehicles can include suitable viscosity enhancing agents, pH adjusting agents, stabilizers, fragrances, etc., as known in the art of topical formulations.

An effective dosage and treatment protocol can be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can extrapolate doses for efficacy and avoidance of toxicity to other species, including humans.

Before human studies of efficacy are undertaken, Phase I clinical studies in normal subjects can help establish safe doses. Numerous factors can be taken into consideration by a clinician when determining an optimal dosage for a given subject. Primary among these is the toxicity and half-life of the chosen compound. Additional factors include the size of the patient, the age of the patient, the general condition of the patient, the particular disease, condition, or disorder being treated, the severity of the disease, condition,. or disorder being treated, the presence of other drugs in the patient, the effect desired, and the like. The trial dosages would be chosen after consideration of the results of animal studies and the clinical literature.

One of ordinary skill in the art will appreciate that the endpoint of treatment chosen in a particular case will vary according to the disease, condition, or disorder being treated, the outcome desired by the patient, subject, or treating physician, and other factors. Where the composition is being used to lighten skin color such as, for example, to reverse hyperpigmentation caused by, for example, inflammation or diseases such as melasma, or to lighten hair color, any one of a number of endpoints can be chosen. For example, endpoints can be defined subjectively such as, for example, when the subject is simply "satisfied" with the results of the treatment. For pharmacological compositions, the endpoint can be determined by the patient's, or the treating physician's, satisfaction with the results of the treatment. Alternatively, endpoints can be defined objectively. For example, the patient's or subject's skin or hair in the treated area can be compared to a color chart. Treatment is terminated when the color of the skin or hair in the treated area is similar in appearance to a color on the chart. Alternatively, the reflectance of the treated skin or hair can be measured, and treatment can be terminated when the treated skin or hair attains a specified reflectance. Alternatively, the melanin content of the treated hair or skin can be measured. Treatment can be terminated when the melanin content of the treated hair or skin reaches a specified value. Melanin content can be determined in any way known to the art, including by histological methods, with or without enhancement by stains for melanin.

In the depigmenting compositions according to the present invention, the concentration of the active compound of the invention is generally between 0.01 and 10%, preferably between 0.1 and 10%, relative to the total weight of the composition.

The compositions of this invention can optionally also contain a moistener, a surfactant, keratolytic, an anti-inflammatory agent, a complexing agent, an antioxidant, a preservative, a colorant, a fragrance, or a sunscreen.

The compositions of the present invention can be applied directly to the skin. Alternatively, they can be delivered by various transdermal drug-delivery systems, such as transdermal patches as known in the art. For example, for topical administration, the active ingredient can be formulated in a solution, gel, lotion, ointment, cream, suspension, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos. Actual methods for preparing topical formulations are known or apparent to those skilled in the art, and are described in detail in *Remington's Pharmaceutical Sciences*, 1990 (supra); and *Pharmaceutical Dosage Forms and Drug Delivery Systems*, 6th ed., Williams & Wilkins (1995).

In order to enhance the percutaneous absorption of the active ingredients, one or more of a number of agents can be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

A topically applied composition of the invention contains a pharmaceutically effective agent that lightens skin as described herein, and those ingredients as are necessary for use as a carrier, such as an emulsion, a cream, an ointment, an aqueous solution, a lotion or an aerosol. Non-limiting examples of such carriers are described in more detail below and may be found in International Patent Publication WO 00/62742, published Oct. 26, 2000; U.S. Pat. No. 5,691,380 to Mason et al., issued Nov. 25, 1997; U.S. Pat. No. 5,968,528 to Deckner et al., issued Oct. 19, 1999; U.S. Pat. No. 4,139,619 to Chidsey, III, issued Feb. 13, 1979; and U.S. Pat. No. 4,684,635 to Orentreich et al., issued Aug. 4, 1987; which are incorporated herein by reference. Suitable pharmaceutical carriers are further described in *Remington's Pharmaceutical Sciences*, 17th ed., Mack Publishing Company, Easton, Pa. (1990), which is a standard reference text in this field.

The pharmaceutical compositions of the invention may optionally include components suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds of the invention. The *CTFA Cosmetic Ingredient Handbook*, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin and bisabolol and dipotassium glycyrrhizinate), skin treating agents, thickeners, and vitamins and derivatives thereof.

In addition to the pharmaceutically effective amount of an agent disclosed herein, the topical compositions of the present invention also comprise a dermatologically acceptable carrier. The phrase "dermatologically acceptable carrier", as used herein, means that the carrier is suitable for topical application to the skin, i.e., keratinous tissue, has good aesthetic properties, is compatible with the active agents of the present invention and any other components, and will not cause any safety or toxicity concerns. A safe and effective amount of carrier is from about 50% to about 99.99%, preferably from about 80% to about 99.9%, more preferably from about 90% to about 98%, and most preferably from about 90% to about 95% of the composition.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560 to Dickert et al., issued Aug. 28, 1973; U.S. Pat. No. 4,421,769 to Dixon, et al., issued Dec. 20, 1983; and McCutcheon's Detergents and Emulsifiers, North American Edition, pages 317–324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less than about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g. mineral oil, vegetable oils, synthetic oils, semisynthetic oils, etc..

Useful topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Non-limiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner et al., issued Dec. 17, 1991; and U.S. Pat. No. 5,073,372, to Turner et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See McCutcheon's. *Detergents and Emulsifiers* (1986), supra; U.S. Pat. No. 5,011,681 to Ciotti et al., issued Apr. 30, 1991; U.S. Pat. No. 4,421,769 to Dixon et al. issued Dec. 20, 1983; and U.S. Pat. No. 3,755,560 to Dickert et al., issued Aug. 28, 1973. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued Sep. 29, 1992; U.S. Pat. No. 5,151,210 to Steuri et al. issued Sep. 29, 1992; U.S. Pat. 5,120,532 to Wells et al, issued Jun. 9, 1992; U.S. Pat. No. 4,387,090 to Bolich Jr., issued Jun. 7, 1983; U.S. Pat. No. 3,155,591 to Hilfer, issued Nov. 3, 1964; U.S. Pat. No. 3,929,678 to Laughlin et al, issued Dec. 30, 1975; U.S. Pat. No. 3,959,461 to Bailey et al., May 25, 1976; *McCutcheon's, Detergents & Emulsifiers* (North American edition 1979) M.C. Publishing Co.; and Schwartz, et al., *Surface Active Agents, Their Chemistry and Technology*, New York: Interscience Publishers, 1949.

Alternatively, other useful cationic emulsifiers include amino-amides. Non-limiting examples of these cationic emulsifiers include stearamidopropyl PG-dimonium chloride phosphate, behenamidopropyl PG dimonium chloride, stearamidopropyl ethyidimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water-insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, *Cosmetics, Science and Technology*, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

Ointments of the present invention may comprise a simple carrier base of animal or vegetable oils or semi-solid hydrocarbons (oleaginous); absorption ointment bases, which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and a pharmaceutically effective amount of an agent described herein.

By way of non-limiting example, 1000 g of topical cream is prepared from the following types and amounts of ingredients: a pharmaceutically effective amount of an agent disclosed herein, tegacid regular (150 g) (a self-emulsifying glyceryl monostearate-from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 gm. The tegacid and spermaceti are melted together at a temperature of 70–80° C. The methylparaben is dissolved in about 500 g. of water and the propylene glycol, polysorbate 80, and active compound are added in turn, maintaining a temperature of 75–80° C. The methylparaben mixture is added slowly to the tegacid and spermaceti melt, with constant stirring. The addition is continued for at least 30 minutes with additional stirring until the temperature has dropped to 40–45° C. Finally, sufficient water is added to bring the final weight to 1000 g. and the preparation stirred to maintain homogeneity until cooled and congealed.

By way of non-limiting example, 1000 g of a topical ointment is prepared from the following types and amounts of ingredients: a pharmaceutically effective amount of an agent disclosed herein, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The pharmaceutically effective amount of an agent disclosed herein, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment containing a pharmaceutically effective amount of an agent disclosed herein is prepared from the following types and amounts of ingredients: a pharmaceutically effective amount of an agent disclosed herein, light liquid petrolatum (250 g), wool fat (200 g), and enough white petrolatum to reach 1000 g. Briefly, the pharmaceutically effective amount of an agent disclosed herein is finely divided and added to the light liquid petrolatum. The wool fat and white petrolatum are melted together, strained, and the temperature adjusted to 45–50° C. The liquid petrolatum slurry is added, and the ointment stirred until congealed.

By way of non-limiting example, 1000 ml of an aqueous solution containing a pharmaceutically effective amount of an agent disclosed herein is prepared from the following types and amounts of ingredients: a pharmaceutically effective amount of an agent disclosed herein, polyethylene glycol 4000 (120 g) myristyl-gamma-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a pharmaceutically effective amount of an agent disclosed herein is prepared from the following types and amounts of ingredients: a pharmaceutically effective amount of an agent disclosed herein, N-methyl pyrolidone (40 g), and enough propylene glycol to reach 1000 g.

By way of non-limiting example, an aerosol containing a pharmaceutically effective amount of an agent disclosed herein is prepared from the following types and amounts of materials: a pharmaceutically effective amount of an agent disclosed herein, absolute alcohol (4.37 g), dichlorodifluoroethane (1.43 g) and dichlorotetrafluoroethane (5.70 g). Briefly, the pharmaceutically effective amount of an agent disclosed herein is dissolved in the absolute alcohol and the resulting solution filtered to remove particles and lint. This solution is chilled to about minus 30° C. Then, to this is added the chilled mixture of dichlorodifluoromethane and dichlorotetrafluoroethane.

For oral administration, gelatin capsules or liquid-filled soft gelatin capsules can contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5–15% polysorbate 80 or lecithin, suitable stabilizing agents and, if necessary, buffer substances. Anti-oxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

Additional examples of particular formulations comprising an active compound of the present invention are provided below.

An example of the preparation of a topical gel follows.

TABLE 1

Topical Gel:

| Ingredient | Percent by Weight |
|---|---|
| Active compound | 0.50 |
| Propylene glycol | 20.00 |

TABLE 1-continued

Topical Gel:

| Ingredient | Percent by Weight |
|---|---|
| Ethanol | 20.00 |
| Carboxyvinyl polymer [Carbomer 940 ™] | 1.00 |
| Hydroxyethyl cellulose | 0.40 |
| Benzyl alcohol | 1.00 |
| Sodium hydroxide 1N | to pH 6 |
| Distilled water | Balance |

The components other than sodium hydroxide are combined to yield a homogeneous dispersion. Addition of sodium hydroxide causes the mixture to gel yielding a ready-to-use semisolid.

An example of the preparation of a topical cream follows.

TABLE 2

Topical Cream:

| Ingredient | Percent by Weight |
|---|---|
| Active compound | 0.50 |
| Stearic acid | 7.00 |
| Stearyl alcohol | 5.00 |
| Cetyl alcohol | 2.00 |
| Glycerin | 10.00 |
| Sodium laurylsulfate | 1.00 |
| Propylparaben | 0.05 |
| Methylparaben | 0.25 |
| Disodium edetate | 0.05 |
| Distilled water | Balance |

The first four ingredients are heated to approximately 70° C. to produce a uniform melt. The remaining ingredients are combined, heated to approximately 75° C., and added with mixing to the previously prepared melt. The emulsion thus formed is subsequently homogenized and cooled to yield a smooth white cream.

An example of the preparation of a topical lotion follows.

TABLE 3

Topical Lotion:

| Ingredient | Percent by Weight |
|---|---|
| Active compound | 0.50 |
| Glyceryl monostearate | 1.00 |
| Isopropyl palmitate | 4.00 |
| Polyethylene glycol 400 distearate | 2.00 |
| Glycerin | 10.00 |
| Methylparaben | 0.10 |
| Sodium cetylsulfate | 5.00 |
| Distilled water | Balance |

The first four ingredients are combined and heated to approximately 70° C., then added with agitation to a mixture of the remaining ingredients, also at about 70° C. The emulsion is appropriately homogenized and cooled to produce a smooth, white, pourable lotion.

An example of the preparation of a topical solution follows.

TABLE 4

Topical Solution:

| Ingredient | Percent by Weight |
|---|---|
| Active compound | 0.50 |
| Propylene glycol | 20.00 |
| Ethanol | 50.00 |
| Benzyl alcohol | 1.00 |
| Disodium edetate | 0.01 |
| Propyl gallate | 0.10 |
| Citric acid | 0.20 |
| Sodium hydroxide 1N | to pH 6 |
| Distilled water | Balance |

All ingredients except sodium hydroxide are combined with agitation, and the pH of the resultant solution is adjusted with 1N sodium hydroxide, to pH 6, to yield a free-flowing, quick-drying topical solution.

The topical formulations presented herein are examples of typical gel, cream, lotion, or solution dosage forms of active compounds for use in lightening skin. Other optional components can be added or excipient ratios can be adjusted to enhance cosmetic acceptability of the formulations. Additionally, these alterations can be made to customize the composition toward a particular active compound, for example, to ensure solubilization or to enhance chemical or physical stability. Optional components would include viscosity adjusters such as celluloses, emollient oils such as mineral oil or glycerides, humectants such as polyols, cosolvents such as isopropyl alcohol or acetone, emulsifying agents of the anionic, cationic and non-ionic types, preservatives, antioxidants, opacifiers, colorants and perfumes.

An example of the preparation of an oral tablet formulation follows.

TABLE 5

Tablet Formulation:

| Ingredient | Amount (mg) |
|---|---|
| Active Compound | 25 |
| Lactose | 50 |
| Cornstarch (for mix) | 10 |
| Cornstarch (paste) | 10 |
| Magnesium stearate (1%) | 5 |
| Total | 100 |

The active compound, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet.

An example of the preparation of an oral solution follows.

TABLE 6

Oral Solution:

| Ingredient | Percent by Weight |
|---|---|
| Active Compound | 2.0 |
| Ethyl alcohol | 10.0 |
| Benzyl alcohol | 1.0 |

TABLE 6-continued

Oral Solution:

| Ingredient | Percent by Weight |
| --- | --- |
| Peppermint flavor | 0.2 |
| Vanillin | 0.2 |
| Polysorbate 40 | 0.1 |
| Sucrose | 50.0 |
| Purified water | Balance |

The ingredients are combined and mixed to form a uniform solution.

As will be understood by those in the art, the compositions and pharmaceutical compositions of the invention may be provided as part of a kit. Kits of the present invention comprise a container comprising one or more specific compounds and/or pharmaceutical compositions of the present invention that lighten skin. The container is designed to prevent contamination, minimize evaporation or drying of the composition, etc. Optionally, the kit further comprises printed instructions as a label or package insert directing the use of the enclosed compound or composition to lighten skin pigmentation. The compound or composition may or may not be provided in a preset unit dose or usage amount.

The ability of compounds of formula I to inhibit tyrosinase may be determined using any of the following procedures.

1. Tyrosinase (DOPA Oxidase) Assay Using Cell Lysate:

Human melanoma cell line, SKMEL 188 (licensed from Memorial Sloan-Kettering), is used in the cell lysate assay and the screen. In the assay, compounds and L-dihydroxyphenylalanine (L-DOPA) (100 µg/ml) are incubated with the cell lysates containing human tyrosinase for 8 hrs before the plates are read at 405 nm. Most of the compounds of formula I that were tested in this assay exhibited an $IC_{50}$ of 10 µM or less. For example, the compound of Example 14 below, i.e., N-[trans-4-(2,4-Dihydroxyphenyl)cyclohexyl]-4-methylbenzene sulfonamide, had an $IC_{50}$ in this assay of about 4 µm.

2. Melanin Assay in Human Primary Melanocytes:

Compounds are incubated with human primary melanocytes in the presence of α-melanocyte stimulating hormone (α-MSH) for 2–3 days. Cells are then lysed with sodium hydroxide and sodium dodecyl sulfate (SDS) and melanin signals are read at 405 nm. Alternatively, $^{14}$C-DOPA is added to the cells in combination with tyrosinase inhibitors and acid-insoluble $^{14}$C-melanin is quantitated by a scintillation counter. $IC_{50}$'s reflect the inhibitory potency of the compounds in the new melanin synthesis that was stimulated by α-MSH.

3. Tyrosine Kinase Assay (TK):

TK assays can be performed using purified tyrosine kinase domains of c-met, erb-B2, or IGF-r. A specific antibody against phosphorylated tyrosine residue is used in the assay. Colorimetric signals are generated by horseradish peroxidase, which is conjugated to the antibody.

4. Human Skin Equivalent Model:

A mixture of human melanocytes and keratinocytes is grown in an air-liquid interphase. This tissue culture forms a three-dimensional structure that histologically and microscopically resembles the human skin epidermis. Test compounds are added on top of the cells to mimic topical drug application. After incubation with the compounds (10 µM) for 3 days, the cells are washed extensively and lysed for DOPA oxidase assay.

5. IL-1 Assay (Interleukin-1 Assay):

An IL-1α ELISA assay (R&D system) can be used to evaluate the effect of compounds on IL-1 secretion in a human skin equivalent model. IL-1α is a pro-inflammatory cytokine and plays a role in UV-induced skin inflammation.

6. In Vivo Study:

Black or dark brown guinea pigs with homogeneous skin color can be used in this study. A solution of the test compound of formula I (5% in ethanol:propylene glycol, 70:30) and the vehicle control are applied to the animals twice daily, 5 days per week for 4–8 weeks. Using this assay, depigmentation can be determined by subtracting the light reflectance of untreated skin from the light reflectance of treated skin.

The present invention is illustrated by the following examples. It will be understood, however, that the invention is not limited to the specific details of these examples. Melting points are uncorrected. Proton nuclear magnetic resonance spectra (400 MHz $^1$H NMR) were measured for solutions in $d_6$-DMSO, CDCl$_3$, or $d_4$-MeOH, and peak positions are expressed in parts per million (ppm) downfield from tetramethylsilane (TMS). The peak shapes are denoted as follows: s, singlet; d, doublet; t, triplet; q, quartet, m, multiplet, b, broad.

The acronym PE refers to petroleum ether (B.p.=60–80° C.), HATU stands for O-(7-azabenzotriazol-1-yl)-N,N,N', N'-tetramethyluronium hexafluorophosphate. Flash column chromatography (FCC) was carried out on SiO$_2$. RP-HPLC refers to preparative reverse-phase high-performance liquid chromatography. Mass spectra were obtained using an electrospray ionisation.

The following examples are illustrative only, and are not intended to limit the scope of the present invention.

EXAMPLES

Preparation 1

3(Benzyloxy)-2-cyclohexen-1-one

To a flask equipped with magnetic stirrer and Dean Stark apparatus was added 1,3-cyclohexanedione (70.0 g, 624 mmol), toluene (500 ml), ptoluenesulfonic acid monohydrate (1.68 g, 8.83 mmol) and benzyl alcohol (65.6 g, 606 mmol). The resulting solution was heated under reflux for 2 hr. The reaction mixture was cooled to room temperature and washed with saturated aqueous sodium carbonate solution (4×50 ml). The organic layer was washed with brine (50 ml), dried over magnesium sulfate, filtered and concentrated in vacuo, affording a brown oil which crystallised upon standing. The crude crystalline material was triturated in isopropyl ether (100 ml) and stirred at 0° C. for 2 hr. The mixture was filtered and the crystalline material was washed with ice cold isopropyl ether (3×100 ml) followed by cold petroleum ether (100 ml). The resulting solid was dried overnight under reduced pressure to furnish the title compound (85.3 g, 68%). m/z (ES$^+$) 203 (M+H$^+$).

Preparation 2

(±)-3-(Benzyloxy)-6-(8-hydroxy-1,4-dioxaspiro[4.5]dec-8-yl)-2-cyclohexen-1-one

To a flask equipped with magnetic stirrer was added tetrahydrofuran (600 ml) and diisopropylamine (38.1 ml, 272 mmol). The stirred solution was cooled to −78° C. and n-butyl lithium (113.4 ml, 272 mmol, 2.4 M in hexanes) was added dropwise via syringe. The resulting yellow solution was stirred for 35 min at −78° C., then 3-(benzyloxy)-2-cyclohexen-1-one (50.0 g, 248 mmol) was added as a solution in tetrahydrofuran (100 ml). The solution was stirred for 1 hr prior to the addition of cyclohexane-1,4-dione monoethylene ketal (38.7 g, 248 mmol) as a solution in anhydrous tetrahydrofuran (100 ml). The solution was stirred for 2 hr at −78° C., then allowed to warm slowly to room temperature over 1 hr. Saturated aqueous ammonium chloride (80 ml) was added, followed by dichloromethane (700 ml) and the mixture stirred until no solids remained. The layers were separated and the aqueous phase extracted with dichloromethane (2×100 ml). The combined organic layers were washed with brine (50 ml), dried over magnesium sulfate, then concentrated in vacuo. Trituration of the resulting solid with methanol afforded the title compound (78.4 g, 88%). m/z (ES$^+$) 359 (M+H$^+$).

Preparation 3

(±)-1-(Benzyloxy)-6-bromo-3-(1,4-dioxaspiro[4.5] dec-8-yl)-2-oxabicyclo [2.2.2]octan-5-one A round bottomed flask equipped with magnetic stirrer was charged with (±)-3-(benzyloxy)-6-(8-hydroxy-1,4-dioxaspiro[4.5]dec-8-yl)-2-cyclohexen-1-one (78.4 g, 219 mmol) and dichloromethane (600 ml). To the stirred solution was added N-bromosuccinimide (40.9 g, 230 mmol) in one portion, followed by aqueous hydrobromic acid (3 drops, 48% aqueous solution). The resulting solution was stirred at room temperature for 2 hr, then poured into a separating funnel containing aqueous sodium metabisulfite solution (150 ml) and dichloromethane (200 ml). The layers were separated and the organic layer was washed with brine (200 ml), dried over magnesium sulfate, filtered, then concentrated in vacuo to give a solid. Trituration with methanol (500 ml) afforded the title compound (82.8 g, 86%) as a white solid. m/z (ES$^+$) 437 and 439 [(1:1), M+H$^+$].

Preparation 4

5-(Benzyloxy)-2-(1,4-dioxaspiro[4.5]dec-7-en-8-yl) phenol

A round bottomed flask was charged with (±)-1-(benzyloxy)-6-bromo-3-(1,4-dioxaspiro[4.5]dec-8-yl)-2-oxabicyclo[2.2.2]octan-5-one (36 g, 82.4 mmol) and anhydrous N,N-dimethylformamide (300 ml). To the stirred solution was added 1,8-diazabicyclo[5.4.0]undec-7-ene (13.6 ml, 90.6 mmol) in one portion before heating to 140° C. for 19 hr with vigorous stirring. The reaction mixture was allowed to cool to room temperature and most of the solvent was removed under reduced pressure. The remaining oil was partitioned between dichloromethane (500 ml) and water (100 ml), and the layers were separated. The organic phase was washed with water (2×100 ml) followed by brine (100 ml). The organic phase was dried over magnesium sulfate, filtered and concentrated in vacuo to afford a brown solid. Purification via FCC (SiO$_2$, dichloromethane then ethyl acetate/petroleum ether, 3:7, v/v) furnished an off white solid which was slurried in methanol (150 ml), filtered and washed with methanol (50 ml). The title compound (18.2 g, 65%) was isolated as a white solid after removal of excess solvent under reduced pressure. m/z (ES$^+$) 339(M+H$^+$).

Preparation 5

4-(1,4-Dioxaspiro[4.5]dec-8-yl)-1,3-benzenediol

A flask equipped with magnetic stirrer was charged with 5-(benzyloxy)-2-(1,4-dioxaspiro[4.5]dec-7-en-8-yl)phenol (14.5 g, 42.8 mmol) and tetrahydrofuran (50 ml) and ethanol (100 ml) and palladium (4.54 g, 10% on activated carbon) were added sequentially. The reaction vessel was then evacuated, placed under a hydrogen atmosphere and stirred vigorously for 24 hr. The reaction mixture was filtered through a celite plug, washing with ethyl acetate. The filtrate was concentrated in vacuo to give an off white solid. The crude solid was slurried in dichloromethane (200 ml), affording the title compound (10.2 g, 95%) as a white solid. m/z(ES$^+$) 251(M+H$^+$).

Preparation 6

4-(2,4-Dihydroxyphenyl)cyclohexanone

A flask equipped with magnetic stirrer was charged with 4-(1,4-dioxaspiro[4.5]dec-8-yl)-1,3-benzenediol (11.3 g, 45.2 mmol), acetone (250 ml) and water (50 ml). To the stirred solution was added pyridinium ptoluenesulfonate (1.14 g, 4.52 mmol) in one portion and the reaction mixture was then heated under reflux for 8 hr. After allowing the reaction mixture to cool to room temperature, most of the acetone was removed in vacuo and the remaining mixture was partitioned between ethyl acetate (200 ml) and water (50 ml). The aqueous layer was extracted with ethyl acetate (3×50 ml) and the combined organic layers were washed with brine (30 ml), dried (MgSO$_4$), filtered and concentrated under reduced pressure to afford an off-white powder. After washing the powder with dichloromethane (100 ml) and removal of excess solvent under reduced pressure, the title compound (9.30 g, 100%) was obtained as an off-white powder. m/z (ES$^+$) 207 (M+H$^+$).

Preparation 7

4-(2,4-Bis{[tert-butyl(dimethyl)silyl]oxy}phenyl) cyclohexanone 4-(2,4-Dihydroxyphenyl)cyclohexanone (400 mg) was dissolved in dimethylformamide (3 ml) with stirring. tert-Butyldimethylsilyl chloride (704 mg), imidazole (660 mg) and 4-dimethylaminopyridine (3 mg) were added sequentially. After 4 hr, the solvent was removed in vacuo and the residue partitioned between ethyl acetate (20 ml) and water (5 ml). The aqueous phase was extracted with ethyl acetate (2×10 ml), and the combined organic phases were washed with brine (10 ml), dried (MgSO$_4$), and concentrated under reduced pressure to give a brown oil. Purification via FCC (SiO$_2$ eluting with ethyl acetate/petroleum ether, 1:9 v/v) furnished the title compound as white flakes (750 mg, 89%). $\delta_H$ (CDCl$_3$): 0.18 (6H, s), 0.20 (6H, s), 0.97 (9H, s), 1.03 (9H, s), 1.72–1.87 (2H, m), 2.15–2.17 (2H, m), 2.42–2.48 (4H, m), 3.33 (1H, tt), 6.32 (1H, d), 6.39 (1H, dd), 6.94 (1H, d).

Preparation 8 cis-N-Benzyl-N-[4-(2,4-bis{[tert-butyl(dimethyl) silyl]oxy}phenyl)cyclohexyl]amine To a flask equipped with magnetic stirrer was loaded 4-(2,4-bis{[tert-butyl(dimethyl)silyl]oxy}phenyl) cyclohexanone (3.20 g, 7.36 mmol). Anhydrous 1,2-dichloroethane (85 ml) was added, followed by benzylamine (0.97 ml, 8.83 mmol) as a solution in 1, 2-dichloroethane (20 ml). Activated powdered 4 Å molecular sieves (5.80 g) were added and the reaction mixture stirred vigorously for 2.5 hr. Tetramethylammoniumtriacetoxyborohydride (2.90 g, 11.0 mmol) was added in one portion and the reaction mixture stirred for 64 hr. Aqueous sodium hydroxide solution (30 ml, 0.4M) was added and vigorous stirring was continued for 0.5 hr. The reaction mixture was then filtered through celite, washing with dichloromethane (100 ml). The layers were separated and the aqueous layer was extracted with dichloromethane (2×50 ml). The combined organic phases were washed with brine (100 ml), dried (MgSO$_4$), filtered and concentrated in vacuo affording the crude product. Purification via FCC (SiO$_2$, ethyl acetate/petroleum ether, gradient elution using 1:9, 1:4, then 3:7 v/v) furnished the title compound (2.69 g, 70%) as a pale yellow oil. $\delta_H$(CDCl$_3$) 0.01 (6H, s), 0.05 (6H, s), 0.77 (9H, s), 0.83 (9H, s), 1.31 (1H, br), 1.39 (4H, m), 1.52 (2H, m), 1.70 (2H, m), 2.69 (1H, m), 2.75 (1H, m), 6.10 (1H, d), 6.23 (1H, dd), 6.84 (1H, d), 7.15 (5H, m).

Preparation 9

N-Benzyl-N-[4-(2,4-bis{[tert-butyl(dimethyl)silyl]oxy}phenyl) cyclohexylidene]amine To a flask equipped with magnetic stirrer was added 4-(2,4-bis{[tert-butyl(dimethyl)silyl]oxy}phenyl) cyclohexanone (817 mg, 1.88 mmol). Dichloromethane (50 ml) was added followed by benzylamine (0.82 ml, 7.52 mmol) and activated 4 Å molecular sieves (10.0 g). The reaction mixture was stirred vigorously for 15 hr, then dichloromethane (50 ml) was added and the reaction mixture filtered through celite, washing with dichloromethane (50 ml). The filtrate was concentrated in vacuo affording the title compound (1.00 g, 86%) as a yellow oil. $\delta_H$(CDCl$_3$) 0.19 (6H, s), 0.26 (6H, s), 0.98 (9H, s), 1.03 (9H, s), 1.51 (1H, m), 1.72 (1H, m), 2.03 (2H, m), 2.45 (1H, m), 2.60 (1H, m), 3.04 (1H, m), 3.22 (1H, m), 4.55 (1H, d), 4.60 (1H, d), 6.31 (1H, d), 6.41 (1H, dd), 6.93 (1H, d), 7.33 (5H, m).

Preparation 10 trans-N-Benzyl-N-[4-(2,4-bis{[tert-butyl(dimethyl) silyl]oxy}phenyl)cyclohexyl]amine To a flask equipped with magnetic stirrer was added N-benzyl-N-[4-(2,4-bis{[tert-butyl(dimethyl)silyl]oxy}phenyl)cyclohexylidene]amine (4.00 g, 7.63 mmol) and tetrahydrofuran (480 ml) followed by methanol (120 ml). To the solution was added sodium borohydride (1.16 g, 30.5 mmol) and the reaction mixture stirred for 17 hr. The reaction mixture was then diluted with diethyl ether (600 ml) and aqueous sodium hydroxide (400 ml, 0.4M) was added. After stirring for 10 min, the layers were separated and the aqueous layer extracted with dichloromethane (3×100 ml). The combined organic phases were washed with brine (50 ml), dried over magnesium sulfate and concentrated in vacuo. Purification via FCC (SiO$_2$, ethyl acetate/petroleum ether, gradient elution using 1:9, 1:4, then 3:7, v/v) furnished the title compound as a cream solid (2.09 g, 54%). $\delta_H$(CDCl$_3$) 0.01 (6H, s), 0.05 (6H, s), 0.80 (9H, s), 0.85 (9H, s), 1.18 (4H, m), 1.66 (2H, m), 1.87 (2H, m), 2.19 (1H, m), 2.68 (1H, M), 6.12 (1H, d), 6.23 (1H, dd), 6.77 (1H, d), 7.17 (5H, m).

Preparation 11 trans-4-(2,4-Bis{[tert-butyl(dimethyl)silyl]oxy}phenyl)cyclohexylamine

To a flask was added trans-N-benzyl-N-[4-(2,4-bis{[tert-butyl(dimethyl)silyl]oxy}phenyl) cyclohexyl]amine (500 mg, 0.95 mmol) and ethanol (20 ml). To the stirred solution was added palladium (10% w/w on activated carbon, 200 mg, 0.19 mmol) as a slurry in ethanol (5 ml). The reaction vessel was evacuated, then placed under hydrogen. The reaction mixture was stirred vigorously under an atmosphere of hydrogen for 18 hr, then filtered through a celite plug, washing with methanol (100 ml). The solvent was removed in vacuo affording the title compound (402 mg, 97%) as a colourless oil. $\delta_H$(CDCl$_3$) 0.01 (6H, s), 0.05 (6H, s), 0.78 (9H, s), 0.82 (9H, s), 1.08 (2H, m), 1.21 (2H, m), 1.62 (2H, m), 1.78 (2H, m), 2.59 (2H, m), 6.11 (1H, d), 6.22 (1H, dd), 6.78 (1H, d).

Preparation 12 cis-4-(2,4-bis{[tert-butyl(dimethyl)silyl]oxy}phenyl) cyclohexylamine

To a flask equipped with magnetic stirrer was added cis-N-benzyl-N-[4-(2,4-bis{[tert-butyl(dimethyl)silyl]oxy}phenyl)cyclohexyl]amine (700 mg, 1.33 mmol) and ethanol (30 ml). To the stirred solution was added palladium (10% w/w on activated carbon, 283 mg, 0.27 mmol) as a slurry in ethanol (5 ml). The reaction vessel was evacuated then placed under hydrogen. The reaction mixture was stirred vigorously under an atmosphere of hydrogen for 18 hr then filtered through a celite plug, washing with methanol (100 ml). The solvent was removed in vacuo affording the title compound (561 mg, 97%) as a colourless oil. $\delta_H$(CDCl$_3$) 0.01 (6H, s), 0.04 (6H, s), 0.78 (9H, s), 0.83 (9H, s), 1.21–1.55 (10H, m), 2.64 (1H, m), 3.05 (1H, m), 6.11 (1H, d), 6.22 (1H, dd), 6.84 (1H, d).

Preparation 13

N-[cis-4-(2,4-Bis{[tert-butyl(dimethyl)silyl]oxy}phenyl)cyclohexyl]benzenesulfonamide Method A: To a solution of Preparation 12 (i.e., cis-4-(2,4-bis{[tert-butyl(dimethyl)silyl]oxy}phenyl) cyclohexylamine (200 mg, 459 μmol) and benzenesulfonyl chloride (71 μl, 557 μmol) in DCE (25 mL) was added NEt$_3$ (128 μl, 921 μmol) and DMAP (few crystals). After stirring for 24 hr, the reaction mixture was partitioned between CH$_2$Cl$_2$ (100 ml) and H$_2$O (20 ml) and the aqueous layer extracted with CH$_2$Cl$_2$ (50 ml). The combined organic extracts were washed with brine (50 ml) and dried (MgSO$_4$). Filtration and solvent evaporation gave the title compound (264 mg, quant) as a colourless gum; $\delta_H$ (CDCl$_3$) 0.17 (s, 6H), 0.19 (s, 6H), 0.98 (s, 18H), 1.40–1.80 (m, 8H), 2.78–2.84 (m, 1H), 3.58–3.62 (m, 1H), 4.68 (d, 1H), 6.28 (d, 1H), 6.43 (dd, 1H), 6.96 (d, 1H), 7.49–7.60 (m, 3H), 7.90–7.94 (m, 2H).

Preparation 14

4-Chloro-N-[cis-4-(2,4-Bis{[tert-butyl(dimethyl) silyl]oxy}phenyl)cyclohexyl]benzene sulfonamide From Preparation 12 (65 mg, 149 μmol) and 4-chlorobenzenesulfonyl chloride (39 mg, 185 μmol) following method A to give the title compound (91 mg, quant.) as colourless gum. $\delta_H$ (CDCl$_3$) 0.17 (s, 6H), 0.20 (s, 6H), 0.95 (s, 18H), 1.41–1.79 (m, 8H), 2.75–2.83 (m, 1H), 3.54–3.60 (m, 1H), 5.01 (d, 1H), 6.24 (d, 1H), 6.40 (dd, 1H), 6.92 (d, 1H), 7.44 (d, 2H), 7.83 (d, 2H).

Preparation 15

3-Chloro-N-[cis-4-(2,4-bis{[tert-butyl(dimethyl) silyl]oxy}phenyl)cyclohexyl]-4-fluorobenzenesulfonamide From Preparation 12 (243 mg, 558 μmol) and 3-chloro-4-fluorobenzenesulfonyl chloride (148 mg, 646 μmol) following method A to give the title compound (350 mg, quant.) as yellow solid. $\delta_H$(CDCl$_3$) 0.19 (s, 6H), 0.21 (s, 6H), 0.99 (m, 18H), 1.45–1.84 (m, 8H), 2.79–2.87 (m, 1H), 3.80–3.85 (m, 1H), 4.83 (d, 1H), 6.26 (d, 1H), 6.43 (dd, 1H), 6.92 (1H), 7.28 (t, 1H), 7.77–7.83 (m, 1H), 7.97 (dd, 1H).

Preparation 16

N-[cis-4-(2,4-Bis{[tert-butyl(dimethyl)silyl]oxy}phenyl)cyclohexyl]-2-thiophenesulfonamide From Preparation 12 (243 mg, 558 μmol) and 2-thiophenesulfonyl chloride (172 mg, 940 μmol) following method A to give the title compound (325 mg, quant.) as a tan solid. $\delta_H$(CDCl$_3$) 0.18 (s, 6H), 0.21 (s, 6H), 0.96 (s, 9H), 0.98 (s, 9H), 1.42–1.84 (m, 8H), 2.77–2.84 (m, 1H), 3.64–3.70 (m, 1H), 4.76 (d, 1H), 6.27 (d, 1H), 6.42 (dd, 1H), 6.94 (d, 1H), 7.06 (dd, 1H), 7.56 (dd, 1H), 7.62 (dd, 1H).

Preparation 17

5-Chloro-N-[cis-4-(2,4-bis{[tert-butyl(dimethyl)silyl]oxy}pheny)cyclohexyl]-2-thiophene sulfonamide From Preparation 12 (243 mg, 558 μmol) and 5-chloro-2-thiophenesulfonyl chloride (151 mg, 696 μmol) following method A to give the title compound (343 mg, quant.) as a yellow oil. $\delta_H$ (CDCl$_3$) 0.18 (s, 6H), 0.22 (s, 6H), 0.95 (s, 9H), 0.99 (s, 9H), 1.40–1.84 (m, 8H), 2.78–2.85 (m, 1H), 3.63–3.69 (m, 1H), 4.77 (d, 1H), 6.28 (d, 1H), 6.42 (dd, 1H), 6.90 (d, 1H), 6.94 (d, 1H), 7.40 (d, 1H).

Preparation 18

N-[cis-4-(2,4-Bis{[tert-butyl(dimethyl)silyl]oxy}phenyl)cyclohexyl]-3-nitro benzene sulfonamide From Preparation 12 (243 mg, 558 μmol) and 3-nitrobenzenesulfonyl chloride (136 mg, 614 μmol) following method A to give the title compound (347 mg, quant.) as a yellow oil. $\delta_H$(CDCl$_3$) 0.17 (s, 6H), 0.21 (s, 6H), 0.96 (s, 18H), 1.42–1.79 (m, 8H), 2.77–2.84 (m, 1H), 3.59–3.65 (m, 1H), 4.96 (d, 1H), 6.25 (d, 1H), 6.41 (dd, 1H), 6.93 (d, 1H), 7.64 (t, 1H), 7.83 (dd, 1H), 8.13 (dd, 1H), 8.19 (d, 1H).

Preparation 19

N-[cis-4-(2,4-Bis{[tert-butyl(dimethyl)silyl]oxy}phenyl)cyclohexyl]-4-nitrobenzene sulfonamide From Preparation 12 (180 mg, 413 μmol) and 4-nitrobenzenesulfonyl chloride (110 mg, 614 μmol) following method A to give the title compound (256 mg, quant.) as a yellow oil. $\delta_H$ (CDCl$_3$) 0.19 (s, 6H), 0.21 (s, 6H), 0.98 (s, 18H), 1.40–1.80 (m, 8H), 2.79–2.86 (m, 1H), 3.65–3.71 (m, 1H), 4.83 (d, 1H), 6.28 (d, 1H), 6.42 (dd, 1H), 6.94 (d, 1H), 8.10 (d, 2H), 8.38 (d, 2H).

Preparation 20

N-[cis-4-(2,4-Bis{[tert-butyl(dimethyl)silyl]oxy}phenyl)cyclohexyl]-2,4-dinitrobenzene sulfonamide From Preparation 12 (60 mg, 138 μmol) and 2,4-dinitrobenzenesulfonyl chloride (45 mg, 169 μmol) following method A to give the title compound (92 mg, quant.) as an orange solid. $\delta_H$ (CDCl$_3$) 0.19 (s, 6H), 0.21 (s, 6H), 0.97 (s, 18H), 1.45–1.82 (m, 8H), 2.79–2.87 (m, 1H), 3.80–3.84 (br s, 1H), 5.71–5.80 (br, 1H), 6.26 (d, 1H), 6.42 (dd, 1H), 6.94 (d, 1H), 8.39 (d, 1H), 8.53 (dd, 1H), 8.65 (d, 1H).

Preparation 21

3-Cyano-N-[cis4-(2,4-bis{[tert-butyl(dimethyl)silyl]oxy}phenyl)cyclohexyl]benzene sulfonamide From Preparation 12 (243 mg, 558 μmol) and 3-chlorosulfonylbenzonitrile (124 mg, 615 μmol) following method A to give the title compound (335 mg, quant.) as a yellow gum. $\delta_H$ (CDCl$_3$) 0.17 (s, 6H), 0.20 (s, 6H), 0.98 (s, 18H), 1.41–1.79 (m, 8H), 2.77–2.83 (m, 1H), 3.59–3.64 (m, 1H), 4.96 (d, 1H), 6.24 (d, 1H), 6.41 (dd, 1H), 6.94 (d, 1H), 7.63 (t, 1H), 7.82 (dd, 1H), 8.14 (dd, 1H), 8.19 (d, 1H).

Preparation 22

N-[cis-4-(2,4-Bis{[tert-butyl(dimethyl)silyl]oxy}phenyl)cyclohexyl]-4-(methylsulfonyl)benzenesulfonamide From Preparation 12 (243 mg, 558 μmol) and 4-methylsulfonylbenzenesulfonyl chloride (156 mg, 612 μmol) following method A to give the title compound (365 mg, quant.) as a yellow oil. $\delta_H$ (CDCl$_3$) 0.17 (s, 6H), 0.20 (s, 6H), 0.97 (s, 18H), 1.41–1.79 (m, 8H), 2.77–2.83 (m, 1H), 3.08 (s, 3H), 3.60–3.66 (m, 1H), 4.87 (d, 1H), 6.27 (d, 1H), 6.41 (dd, 1H), 6.93 (d, 1H), 8.09 (s, 4H).

Preparation 23

N-[trans-4-(2,4-Bis{[tert-butyl(dimethyl)silyl]oxy}phenyl)cyclohexyl]benzenesulfonamide From Preparation 11 (497 mg, 1.14 mmol) and benzenesulfonyl chloride (176 μl, 1.37 mmol) following method A to give the title compound (656 mg, quant.) as a yellow solid. $\delta_H$ (CDCl$_3$) 0.17 (s, 6H), 0.20 (s, 6H), 1.24–1.40 (m, 4H), 1.73–1.81 (m, 2H), 1.88–1.97 (m, 2H), 2.68–2.77 (m, 1H), 3.11–3.20 (m, 1H), 4.86 (d, 1H), 6.26 (d, 1H), 6.38 (dd, 1H), 6.86 (d, 1H), 7.46–7.59 (m, 3H), 7.92 (d, 2H).

Preparation 24

N-[cis-4-(2,4-Bis{[tert-butyl(dimethyl)silyl]oxy}phenyl)cyclohexyl]-2-naphthalene sulfonamide From Preparation 12 (44 mg, 100 μmol) and 2-naphthalenesulfonyl chloride (25 mg, 110 μmol) following method A to give the title compound (63 mg, quant.) as a white solid. $\delta_H$(CDCl$_3$) 0.17 (s, 6H), 0.20 (s, 6H), 0.96 (m, 18H), 1.42–1.83 (m, 8H), 2.77–2.85 (m, 1H), 3.79–3.84 (m, 1H), 4.81 (d, 1H), 6.23 (d, 1H), 6.43 (dd, 1H), 6.91 (d, 1H), 7.55–7.65 (m, 2H), 7.84–8.00 (m, 4H), 8.40 (m, 1H).

Preparation 25

N-[cis-4-(2,4-Bis{[tert-butyl(dimethyl)silyl]oxy}phenyl)cyclohexyl]-4-methylbenzene sulfonamide From Preparation 12 (42 mg, 96 μmol) and 4-toluenesulfonyl chloride (37 mg, 194 μmol) following method A to give the title compound (57 mg, quant.) as a white solid. $\delta_H$ (CDCl$_3$) 0.17 (s, 6H), 0.19 (s, 6H), 0.96 (s, 18H), 1.43–1.78 (m, 8H), 2.40 (s, 3H), 2.74–2.81 (m, 1H), 3.51–3.58 (m, 1H), 5.03 (d, 1H), 6.25 (d, 1H), 6.38 (dd, 1H), 6.92 (d, 1H), 7.28 (d, 2H), 7.79 (d, 2H).

Preparation 26

N-[trans-4-(2,4-Bis{[tert-butyl(dimethyl)silyl] oxy}phenyl)cyclohexyl]-4-methylbenzene sulfonamide From Preparation 11 (44 mg, 100 μmol) and 4-toluenesulfonyl chloride (22 mg, 115 μmol) following method A to give the title compound (59 mg, quant.) as a yellow oil. $\delta_H$ (CDCl$_3$) 0.16 (s, 6H), 0.19 (s, 6H), 0.95 (s, 9H), 0.98 (s, 9H), 1.20–1.39 (m, 4H), 1.73–1.80 (m, 2H), 1.90–1.97 (m, 2H), 2.42 (s, 3H), 2.67–2.78 (m, 1H), 3.09–3.20 (m, 1H), 4.41 (d, 1H), 6.26 (d, 1H), 6.37 (dd, 1H), 6.86 (d, 1H), 7.30 (d, 2H), 7.78 (d, 2H).

Preparation 27

N-[cis-4-(2,4-Bis{[tert-butyl(dimethyl)silyl] oxy}phenyl)cyclohexyl]-4-methoxybenzene sulfonamide From Preparation 12 (42 mg, 96 μmol) and 4-methoxybenzenesulfonyl chloride (46 mg, 222 μmol) following method A to give the title compound (58 mg, quant.) as a white solid. $\delta_{H\ (CDCl3)}$ 0.20 (s, 12H), 1.00 (s, 18H), 1.40–1.81 (m, 8H), 2.77–2.84 (m, 1H), 3.52–3.59 (br s, 1H), 3.89 (s, 3H), 4.92 (d, 1H), 6.29 (d, 1H), 6.42 (dd, 1H), 6.96 (d, 1H), 7.33 (d, 2H), 7.80 (d, 2H).

Preparation 28

N-[cis-4-(2,4-Bis{[tert-butyl(dimethyl)silyl] oxy}phenyl)cyclohexyl]-5-(dimethyl-amino)-1-naphthalenesulfonamide From Preparation 12 (44 mg, 100 μmol) and dansyl chloride (30 mg, 110 μmol) following method A to give the title compound (67 mg, quant.) as a yellow solid. $\delta_H$ (CDCl$_3$) 0.16 (s, 6H), 0.20 (s, 6H), 0.95 (m, 18H), 1.45–1.86 (m, 8H), 2.75–2.83 (m, 1H), 3.02 (s, 6H), 3.50–3.55 (m, 1H), 4.75 (d, 1H), 6.20 (d, 1H), 6.40 (dd, 1H), 6.62 (d, 1H), 7.30 (d, 1H), 7.58–7.65 (m, 2H), 8.21 (d, 1H), 8.50 (d, 1H), 8.57 (d, 1H).

Preparation 29

N-[cis-4-(2,4-Bis{[tert-butyl(dimethyl)si lyl] oxy}phenyl)cyclohexyl]-1-methyl-1H-imidazole-4-sulfonamide From Preparation 12 (42 mg, 96 μmol) and 1-methyl-4-chlorosulfonylimidazole (35 mg, 193 μmol) following method A to give the title compound (56 mg, quant.) as a pale yellow oil. $\delta_H$ (CDCl$_3$) 0.17 (s, 6H), 0.19 (s, 6H), 0.95 (s, 9H), 0.97 (s, 9H), 1.48–1.66 (m, 6H), 1.79–1.88 (m, 2H), 2.75–2.82 (m, 1H), 3.54–3.59 (m, 1H), 3.73 (s, 3H), 5.06 (d, 1H), 6.25 (d, 1H), 6.40 (dd, 1H), 6.96 (d, 1H), 7.44 (s, 1H), 7.47 (s, 1H).

Preparation 30

N-[cis-4-(2,4-Bis{[tert-butyl(dimethyl)silyl] oxy}phenyl)cyclohexyl]-5-(3-isoxazolyl)-2-thiophenesulfonyl From Preparation 12 (42 mg, 96 μmol) and 5-(3-isoxazolyl)-2-thiophenesulfonyl chloride (48 mg, 192 μmol) following method A (62 mg, quant.) as a yellow oil. $\delta_H$ (CDCl$_3$) 0.17–0.18 (m, 12H), 0.95–0.97 (m, 18H), 1.51–1.89 (m, 8H), 2.77–2.83 (m, 1H), 3.48–3.55 (m, 1H), 5.20 (d, 1H), 6.27 (d, 1H), 6.39 (dd, 1H), 6.49 (d, 1H), 6.97 (d, 1H), 7.42 (d, 1H), 7.60 (d, 1H), 8.29 (d, 1H).

Preparation 31

Methyl 3-({[cis-4-(2,4-bis{[tert-butyl(dimethyl) silyl]oxy}phenyl)cyclohexyl]amino}sulfonyl) benzoate From Preparation 12 (0.80 g, 1.8 mmol) and methyl 3-chlorosulfonylbenzoate (0.48 g, 2.0 mmol) following method A (i-Pr$_2$NEt employed instead of NEt$_3$) to give the title compound (1.09 g, 94%) as an off-white solid. $\delta_H$ (CDCl$_3$) 0.17 (s, 6H), 0.19 (s, 6H), 0.96 (s, 18H), 1.41–1.78 (m, 8H), 2.73–2.82 (m, 1H), 3.58–3.62 (m, 1H), 3.94 (s, 3H), 5.09 (d, 2H), 6.23 (d, 1H), 6.38 (dd, 1H), 6.92 (d, 1H), 7.60 (t, 1H), 8.09 (dd, 1H), 8.22 (dd, 1H), 8.57 (dd, 1H).

Preparation 32

Methyl 4-({[cis-4-(2,4-bis{[tert-butyl(dimethyl) silyl]oxy}phenyl)cyclohexyl]amino}sulfonyl) benzoate From Preparation 12 (217 mg, 498 μmol) and methyl 4-chlorosulfonylbenzoate (132 mg, 562 μmol) following method A (i-Pr$_2$NEt used instead of NEt$_3$) to give the title compound (295 mg, 93%) as an off-white solid. $\delta_H$ (CDCl$_3$) 0.17 (s, 6H), 0.19 (s, 6H), 0.96 (s, 18H), 1.40–1.76 (m, 8H), 2.75–2.83 (m, 1H), 3.59–3.64 (m, 1H), 3.95 (s, 3H), 5.28 (d, 2H), 6.25 (d, 1H), 6.37 (dd, 1H), 6.91 (d, 1H), 7.99 (d, 2H), 8.16 (d, 2H).

Preparation 33

4-Cyano-N-[trans-4-(2,4-bis{[tert-butyl(dimethyl) silyl]oxy}phenyl)cyclohexyl]benzene sulfonamide From Preparation 11 (350 mg, 803 μmol) and 4-chlorosulfonylbenzonitrile (200 mg, 992 μmol) following method A to give the title compound (482 mg, quant.) as an off-white solid. m/z (ES$^-$) 618 [M+OH]$^-$.

Preparation 34

N-[2-Chloro-4-({[cis-4-(2,4-bis{[tert-butyl (dimethyl)silyl]oxy}phenyl)cyclohexyl] amino}sulfonyl)phenyl]acetamide From Preparation 12 (67 mg, 154 μmol) and 4-acetamido-3-chlorobenzenesulfonyl chloride (64 mg, 239 μmol) following method A (solvent system employed=DCE-THF, 7:1) to give the title compound (103 mg, quant.) as a white solid. $\delta_H$ (CDCl$_3$) 0.18 (s, 6H), 0.21 (s, 6H), 0.98 (m, 18H), 1.42–1.80 (m, 8H), 2.24 (s, 3H), 2.76–2.82 (m, 1H), 3.54–3.60 (m, 1H), 5.03 (d, 1H), 6.24 (d, 1H), 6.39 (dd, 1H), 6.92 (d, 1H), 7.79 (d, 1H), 7.93 (s, 1H), 8.60 (d, 1H).

Preparation 35

N-[trans4-(2,4-Bis{[tert-butyl(dimethyl)silyl] oxy}phenyl)cyclohexyl]-4-fluorobenzene sulfonamide From Preparation 11 (350 mg, 803 μmol) and 4-fluorobenzenesulfonyl chloride (190 mg, 970 μmol) following method A to give the title compound (477 mg, quant.) as an off-white solid. m/z (ES$^-$) 593 [M–H]$^-$.

Preparation 36

N-[trans-4-(2,4-Bis{[tert-butyl(dimethyl)silyl]
oxy}phenyl)cyclohexyl]-2,4-difluorobenzene
sulfonamide From Preparation 11 (350 mg, 803 μmol) and 2,4-difluorobenzenesulfonyl chloride (210 mg, 970 μmol) following method A to give the title compound (450 mg, 92%) as an off-white solid. m/z (ES$^-$) 611 [M−H]$^-$.

Preparation 37

N-[trans-4-(2,4-Bis{[tert-butyl(dimethyl)silyl]
oxy}phenyl)cyclohexyl]-2,3,4,5,6-pentafluoro
benzenesulfonamide From Preparation 11 (350 mg, 803 μmol) and pentafluorobenzenesulfonyl chloride (140 μL, 970 μmol) following method A to give the title compound (450 mg, 84%) as an off-white solid. m/z (ES$^-$) 664 [M−H]$^-$.

Preparation 38

N-[trans-4-(2,4-Bis{[tert-butyl(dimethyl)silyl]
oxy}phenyl)cyclohexyl]-3-(trifluoromethyl)
benzenesulfonamide From Preparation 11 (350 mg, 803 μmol) and 3-trifluoromethylbenzenesulfonyl chloride (160 μL, 970 μmol) following method A to give the title compound (516 mg, quant.) as an off-white solid; m/z (ES$^-$) 642 [M−H]$^-$.

Example 1

N-[cis-4-(2,4-Dihydroxyphenyl)cyclohexyl]
benzenesulfonamide

Method B: Preparation 13 (264 mg, 459 μmol) was dissolved in DCE (50 ml) and treated with H$_2$O (17 ml) and TFA (17 ml). The mixture was heated under gentle reflux for 24 hr and after cooling, toluene (70 ml) added. The solvents were removed under reduced pressure and MeOH (50 ml) added. Following solvent evaporation, a brown oil was isolated which was subjected to FCC (PE-EtOAc, 3:1 to 1:1) to furnish the title compound (102 mg, 64%) as a white solid. $\delta_H$ (CD$_3$OD) 1.48–1.76 (m, 8H), 2.73–2.80 (m, 1H), 3.40–3.44 (m, 1H), 6.22–6.26 (m, 2H), 6.95 (d, 1H), 7.54–7.62 (m, 3H), 7.91 (d, 2H); m/z (ES$^-$) 346 [M−H]$^-$.

Example 2

4-Chloro-N-[cis-4-(2,4-dihydroxyphenyl)
cyclohexyl]benzenesulfonamide

From Preparation 14 (91 mg, 149 μmol) following method B to give the title compound (29 mg, 51%) as a white solid. $\delta_H$ ((CD$_3$)$_2$CO) 1.52–1.81 (m, 8H), 2.79–2.90 (m, 1H), 3.51–3.59 (m, 1H), 6.28 (dd, 1H), 6.35 (d, 1H), 6.70 (d, 1H), 6.97 (d, 1H), 7.63 (d, 2H), 7.88 (s, 1H), 7.91 (d, 2H), 7.99 (s, 1H); m/z (ES$^+$) 382 [M+H]$^+$.

Example 3

3-Chloro-N-[cis-4-(2,4-dihydroxyphenyl)
cyclohexyl]-4-fluorobenzenesulfonamide

From Preparation 15 (350 mg, 557 μmol) following method B to give the title compound (178 mg, 80%) as an off-white solid. $\delta_H$ (CD$_3$OD) 1.58–1.82 (m, 8H), 2.78–2.85 (m, 1H), 3.48–3.52 (br s, 1H), 6.26–6.31 (m, 2H), 6.98 (d, 1H), 7.46 (t, 1H), 7.88–7.93 (m, 1H), 8.06 (dd, 1H); m/z (ES$^-$) 398 [M−H]$^-$.

Example 4

N-[cis-4-(2,4-Dihydroxyphenyl)cyclohexyl]-2-
thiophenesulfonamide

From Preparation 16 (325 mg, 558 μmol) following method B to give the title compound (151 mg, 77%) as a white solid. $\delta_H$ (CD$_3$OD) 1.59–1.87 (m, 8H), 2.79–2.88 (m, 1H), 3.56–3.59 (m, 1H), 6.23–6.25 (m, 2H), 6.99 (d, 1H), 7.17 (dd, 1H), 7.66 (dd, 1H); m/z (ES$^-$) 352 [M−H]$^-$.

Example 5

5-Chloro-N-[cis-4-(2,4-dihydroxyphenyl)
cyclohexyl]-2-thiophenesulfonamide

From Preparation 17 (343 mg, 556 μmol) following method B to give the title compound (153 mg, 71%) as white solid. $\delta_H$ (CD$_3$OD) 1.60–1.88 (m, 8H), 2.80–2.88 (m, 1H), 3.56–3.59 (br s, 1H), 6.23–6.25 (m, 2H), 6.99 (d, 1H), 7.10 (d, 1H), 7.48 (d, 1H); m/z (ES$^-$) 386 [M−H]$^-$.

Example 6

N-[cis-4-(2,4-Dihydroxyphenyl)cyclohexyl]-3-
nitrobenzenesulfonamide

From Preparation 18 (347 mg, 558 μmol) following method B to give the title compound (114 mg, 51%) as a yellow solid. $\delta_H$ (CD$_3$OD) 1.59–1.90 (m, 8H), 2.79–2.86 (m, 1H), 3.55–3.58 (br s, 1H), 6.25–6.30 (m, 2H), 6.98 (d, 1H), 7.85 (t, 1H), 8.32 (d, 1H), 8.50 (d, 1H), 8.77 (s, 1H); m/z (ES$^-$) 391 [M−H]$^-$.

Example 7

N-[cis-4-(2,4-Dihydroxyphenyl)cyclohexyl]-4-
nitrobenzenesulfonamide

From Preparation 19 (256 mg, 413 μmol) following method B to give the title compound (119 mg, 74%) as a white solid. $\delta_H$ (CD$_3$OD) 1.55–1.80 (m, 8H), 2.78–2.86 (m, 1H), 3.53–3.59 (m, 1H), 6.21–6.29 (m, 2H), 6.97 (d, 1H), 8.16 (d, 2H), 8.41 (d, 2H); m/z (ES$^-$) 391 [M−H]$^-$.

Example 8

N-[cis-4-(2,4-Dihydroxyphenyl)cyclohexyl]-2,4-
dinitrobenzenesulfonamide

From Preparation 20 (92 mg, 138 μmol) following method B to give the title compound (26 mg, 43%) as a pale yellow solid. $\delta_H$ (CD$_3$OD) 1.58–1.86 (m, 8H), 2.79–2.86 (m, 1H), 3.76–3.80 (br s, 1H), 6.25–6.30 (m, 2H), 6.99 (d, 1H), 8.41 (d, 1H), 8.64 (dd, 1H), 8.75 (d, 1H); m/z (ES$^-$) 436 [M−H]$^-$.

Example 9

3-Cyano-N-[cis-4-(2,4-dihydroxyphenyl)cyclohexyl]
benzenesulfonamide

From Preparation 21 (335 mg, 558 μmol) following method B to give the title compound (110 mg, 53%) as a white solid. $\delta_H$ (CD$_3$OD) 1.59–1.81 (m, 8H), 2.79–2.85 (m, 1H), 3.51–3.56 (br s, 1H), 6.26–6.30 (m, 2H), 6.98 (d, 1H), 7.79 (t, 1H), 8.00 (d, 1H), 8.21 (d, 1H), 8.29 (s, 1H); m/z (ES$^-$) 371 [M−H]$^-$.

Example 10

N-[cis-4-(2,4-Dihydroxyphenyl)cyclohexyl]-4-(methylsulfonyl)benzenesulfonamide

From Preparation 22 (365 mg, 558 μmol) following method B to give the title compound (158 mg, 66%) as a white solid. $\delta_H$ (CD$_3$OD) 1.51–1.77 (m, 8H), 2.72–2.81 (m, 1H), 3.17 (s, 3H), 3.49–3.52 (br s, 1H), 6.20–6.24 (m, 2H), 6.93 (d, 1H), 8.12 (s, 4H); m/z (ES$^-$) 424 [M–H]$^-$.

Example 11

N-[trans-4-(2,4-Dihydroxyphenyl)cyclohexyl]benzenesulfonamide

From Preparation 23 (656 mg, 1.14 mmol) following method B to give the title compound (310 mg, 78%) as a white solid. $\delta_H$ (CD$_3$OD) 1.32–1.43 (m, 4H), 1.74–1.88 (m, 4H), 2.68–2.77 (m, 1H), 3.05–3.17 (m, 1H), 6.20–6.27 (m, 2H), 6.85 (d, 1H), 7.56–7.66 (m, 3H), 7.92 (d, 2H); m/z (ES$^-$) 346 [M–H]$^-$.

Example 12

N-[cis-4-(2,4-Dihydroxyphenyl)cyclohexyl]-2-naphthalenesulfonamide

Method C: Preparation 24 (63 mg, 100 μmol) was dissolved in CH$_2$Cl$_2$ (6 ml) and treated with H$_2$O (2 ml) and TFA (3 ml). After stirring for 18 hr, the reaction mixture was treated with toluene (30 ml). The solvents were removed under reduced pressure and MeOH (15 ml) added. Following solvent evaporation, a brown gum was obtained which was subjected to FCC (PE-EtOAc, 3:1 to 1:1) to afford the title compound (30 mg, 75%) as a white solid. $\delta_H$ (CD$_3$OD) 1.49–1.78 (m, 8H), 2.70–2.79 (m, 1H), 3.44–3.48 (br s, 1H), 6.21–6.24 (m, 2H), 6.94 (d, 1H), 7.60–7.68 (m, 2H), 7.91 (dd, 1H), 7.95–7.99 (m, 1H), 8.02–8.06 (m, 2H), 8.44 (d, 1H); m/z (ES$^+$) 398 [M+H]$^+$.

Example 13

N-[cis-4-(2,4-Dihydroxyphenyl)cyclohexyl]-4-methylbenzenesulfonamide

From Preparation 25 (57 mg, 96 μmol) following method C to give the title compound (21 mg, 60%) as a white solid. $\delta_H$ (CD$_3$OD) 1.51–1.82 (m, 8H), 2.46 (s, 3H), 2.76–2.83 (m, 1H), 3.41 (br s, 1H), 6.26–6.30 (m, 2H), 6.98 (d, 1H), 7.40 (d, 2H), 7.81 (d, 2H); m/z (ES$^-$) 360 [M–H]$^-$.

Example 14

N-[trans-4-(2,4-Dihydroxyphenyl)cyclohexyl]-4-methylbenzenesulfonamide

From Preparation 26 (59 mg, 100 μmol) following method C to give the title compound (10 mg, 28%) as a white solid. $\delta_H$ (CD$_3$OD) 1.33–1.42 (m, 4H), 1.75–1.84 (m, 4H), 2.47 (s, 3H), 2.67–2.77 (m, 1H), 3.02–3.11 (m, 1H), 6.21–6.28 (m, 2H), 6.85 (d, 1H), 7.41 (d, 2H), 7.80 (d, 2H); m/z (ES$^-$) 360 [M–H]$^-$.

Example 15

N-[cis-4-(2,4-Dihydroxyphenyl)cyclohexyl]-4-methoxybenzenesulfonamide

From Preparation 27 (58 mg, 96 μmol) following method C to give the title compound (21 mg, 58%) as a white solid. $\delta_H$ (CD$_3$OD) 1.55–1.82 (m, 8H), 2.77–2.83 (m, 1H), 3.42 (br s, 1H), 3.91 (s, 3H), 6.27–6.30 (m, 2H), 6.98 (d, 1H), 7.08 (d, 2H), 7.83 (d, 2H); m/z (ES$^+$) 378 [M+H]$^+$.

Example 16

N-[cis-4-(2,4-Dihydroxyphenyl)cyclohexyl]-5-(dimethylamino)-1-naphthalenesulfonamide From Preparation 28 (67 mg, 100 μmol) following method C to give the title compound (20 mg, 45%) as an off-white solid. $\delta_H$ (CD$_3$OD) 1.35–1.70 (m, 8H), 2.68–2.77 (m, 1H), 3.48–3.52 (m, 1H), 6.19–6.23 (m, 2H), 6.62 (d, 1H), 7.33 (d, 1H), 7.59 (t, 1H), 7.64 (t, 1H), 8.25 (d, 1H), 8.53 (d, 1H), 8.58 (d, 1H); m/z (ES$^+$)=441 [M+H]$^+$.

Example 17

N-[cis-4-(2,4-Dihydroxyphenyl)cyclohexyl]-1-methyl-1H-imidazole-4-sulfonamide

From Preparation 29 (56 mg, 96 μmol) following method C to give the title compound (21 mg, 58%) as a white solid. $\delta_H$ (CD$_3$OD) 1.59–1.88 (m, 8H), 2.78–2.85 (m, 1H), 3.58 (br s, 1H), 3.83 (s, 3H), 6.26–6.30 (m, 2H), 6.99 (d, 1H), 7.78 (s, 1H), 7.83 (s, 1H); m/z (ES$^+$) 325 [M+H]$^+$.

Example 18

N-[cis-4-(2,4-Dihydroxyphenyl)cyclohexyl]-5-(3-isoxazolyl)-2-thiophenesulfonamide From Preparation 30 (62 mg, 96 μmol) following method C to give the title compound (15 mg, 38%) as a pale orange solid. $\delta_H$ (CD$_3$OD) 1.59–1.96 (m, 8H), 2.79–2.87 (m, 1H), 3.59–3.66 (br s, 1H), 6.25–6.32 (m, 2H), 6.82 (d, 1H), 6.99 (d, 1H), 7.63 (d, 1H), 7.68 (d, 1H), 8.49 (d, 1H); m/z (ES$^-$) 419 [M–H]$^-$.

Example 19

Methyl 3-({[cis-4-(2,4-dihydroxyphenyl)cyclohexyl]amino}sulfonyl)benzoate

Method D: To a stirred solution of Preparation 31 (196 mg, 309 μmol) in THF (14 ml) was added HOAc (64 μl, 1116 μmol) and TBAF.H$_2$O (324 mg, 1239 ,mol). After 30 min, H$_2$O (30 ml) and EtOAc (30 ml) were added and stirring continued for 10 min. The layers were separated, and the aqueous phase extracted with EtOAc (2×20 ml). The combined organic extracts were washed with brine (30 ml) and dried (MgSO$_4$). Filtration and concentration under reduced pressure furnished a yellow gum that was purified by FCC (PE-EtOAc, 4:1 to 2:3) to yield the title compound (110 mg, 88%) as a white solid. $\delta_H$ ((CD$_3$)$_2$CO) 1.53–1.82 (m, 8H), 2.80–2.90 (m, 1H), 3.54–3.61 (m, 1H), 3.94 (s, 3H), 6.28 (dd, 1H), 6.35 (d, 1H), 6.81 (d, 1H), 6.97 (d, 1H), 7.75 (t, 1H), 7.88 (s, 1H), 7.98 (s, 1H), 8.14 (dd, 1H), 8.22 (dd, 1H), 8.50 (dd, 1H); m/z (ES$^-$) 404 [M–H]$^-$.

Example 20

Methyl 4-({[cis-4-(2,4-dihydroxyphenyl)cyclohexyl]amino}sulfonyl)benzoate

From Preparation 32 (295 mg, 465 μmol) following method D to give the title compound (142 mg, 75%) as a white solid. $\delta_H$ ((CD$_3$)$_2$CO) 1.51–1.80 (m, 8H), 2.80–2.88 (m, 1H), 3.55–3.61 (br, 1H), 3.93 (s, 3H), 6.28 (dd, 1H), 6.35 (d, 1H), 6.81 (d, 1H), 6.97 (d, 1H), 7.88 (s, 1H), 7.98 (s, 1H), 8.02 (d, 2H), 8.18 (d, 2H); m/z (ES$^-$) 404 [M–H]$^-$.

Example 21

Methyl 3-({[trans-4-(2,4-dihydroxyphenyl)cyclohexyl]amino}sulfonyl)benzoate

Method E: A solution of Preparation 11 (150 mg, 344 μmol) and methyl 3-chlorosulfonylbenzoate (97 mg, 414 μmol) in DCE (5 ml) was treated with NEt$_3$ (98 μl, 700 μmol) and DMAP (few crystals) and stirred for 18 hr. The reaction mixture was partitioned between CH$_2$Cl$_2$ (100 ml) and H$_2$O (20 ml), and the aqueous layer extracted with CH$_2$Cl$_2$ (50 ml). The combined organic extracts were washed with brine (50 ml), dried (MgSO$_4$), filtered and concentrated in vacuo. The resulting oil was dissolved in THF (10 ml) and treated with HOAc (100 μl) and TBAF.H$_2$O (360 mg, 1380 μmol). After 30 min, H$_2$O (30 ml) and EtOAc (30 ml) were added, and stirring continued for a further 10 min. The layers were separated, and the aqueous phase was extracted with EtOAc (2×20 ml) before the combined organic extracts were washed with brine (30 ml) and dried (MgSO$_4$). Filtration and concentration under reduced pressure furnished the crude product which was purified by FCC (PE-EtOAc, 4:1 to 2:3) to yield the title compound (110 mg, 78%) as a white solid. $\delta_H$ (CD$_3$OD) 1.24–1.41 (m, 4H), 1.63–1.81 (m, 4H), 2.62–2.73 (m, 1H), 3.05–3.17 (m, 1H), 3.94 (s, 3H), 6.16–6.23 (m, 2H), 6.80 (d, 1H), 7.68 (t, 1H), 8.10 (d, 1H), 8.21 (d, 1H), 8.49 (s, 1H); m/z (ES$^-$) 404 [M−H]$^-$.

Example 22

Methyl 4-({[trans-4-(2,4-dihydroxyphenyl)cyclohexyl]amino}sulfonyl)benzoate

From Preparation 11 (150 mg, 344 μmol) and methyl 4-chlorosulfonylbenzoate (97 mg, 414 μmol) following method E to give the title compound (110 mg, 78%) as a white solid. $\delta_H$ (CD$_3$OD) 1.20–1.41 (m, 4H), 1.70–1.81 (m, 4H), 2.61–2.70 (m, 1H), 3.04–3.18 (m, 1H), 3.92 (s, 3H), 6.15–6.22 (m, 2H), 6.69 (d, 1H), 7.98 (d, 2H), 8.16 (d, 2H); m/z (ES$^+$) 406 [M+H]$^+$.

Example 23

4-Cyano-N-[trans-4-(2,4-dihydroxyphenyl)cyclohexyl]benzenesulfonamide

From Preparation 33 (482 mg, 803 μmol) following method D to give the title compound (210 mg, 70%) as a white solid. $\delta_H$ ((CD$_3$)$_2$SO) 1.28–1.42 (m, 4H), 1.61–1.89 (m, 4H), 2.55–2.63 (m, 1H), 3.04–3.18 (br, 1H), 3.22 (d, 1H), 6.17 (dd, 1H), 6.27 (d, 1H), 6.80 (d, 1H), 8.04 (d, 2H), 8.18 (d, 2H), 8.97 (s, 1H), 9.03 (s, 1H); m/z (ES$^-$) 371 [M−H]$^-$.

Example 24

N-[2-Chloro-4-({[cis-4-(2,4-dihydroxyphenyl)cyclohexyl]amino}sulfonyl)phenyl]acetamide From Preparation 34 (103 mg, 154 μmol) following method D to give the title compound (37 mg, 55%) as a white solid. $\delta_H$ ((CD$_3$)$_2$CO) 1.55–1.81 (m, 8H), 2.23 (s, 3H), 2.80–2.88 (m, 1H), 3.51–3.58 (m, 1H), 6.28 (dd, 1H), 6.35 (d, 1H), 6.66 (d, 1H), 6.96 (d, 1H), 7.82 (dd, 1H), 7.89 (br s, 1H), 7.92 (d, 1H), 7.99 (br s, 1H), 8.49 (d, 1H), 8.85 (br s, 1H); m/z (ES$^+$) 439 [M+H]$^+$.

Example 25

4-Amino-3-chloro-N-[cis-4-(2,4-dihydroxyphenyl)cyclohexyl]benzenesulfonamide

From Preparation 34 (103 mg, 154 μmol) following method B to give the title compound (30 mg, 49%) as a white solid. $\delta_H$ ((CD$_3$)$_2$CO) 1.52–1.63 (m, 4H), 1.67–1.80 (m, 4H), 2.79–2.86 (m, 1H), 3.41–3.49 (m, 1H), 5.67 (br s, 2H); 6.29–6.35 (m, 3H), 6.94–6.99 (m, 2H), 7.55 (dd, 1H), 7.72 (d, 1H), 7.88 (br s, 1H), 7.97 (br s, 1H); $\delta_C$ (CD$_3$OD)= 27.0, 31.3, 35.6, 48.9, 102.2, 106.2, 114.3, 117.2, 124.8, 126.8, 126.9, 128.4, 128.6, 148.4, 155.0, 155.7; m/z (ES$^+$) 397 [M+H]$^+$.

Example 26

4-Acetyl-N-[cis-4-(2,4-dihydroxyphenyl)cyclohexyl]benzenesulfonamide

From Preparation 12 (150 mg, 344 μmol) and 4'-chlorosulfonylacetophenone (90 mg, 412 μmol) following method E to give the title compound (77 mg, 56%) as a white solid. $\delta_H$ (CD$_3$OD) 1.50–1.76 (m, 8H), 2.63 (s, 3H), 2.72–2.80 (m, 1H), 3.44–3.50 (m, 1H), 6.21–6.25 (m, 2H), 6.93 (d, 1H), 8.00 (d, 2H), 8.13 (d, 2H); m/z (ES$^-$) 388 [M−H]$^-$.

Example 27

N-[cis-4-(2,4-Dihydroxyphenyl)cyclohexyl]4-(trifluoromethoxy)benzenesulfonamide

From Preparation 12 (150 mg, 344 μmol) and 4-trifluoromethoxybenzenesulfonyl chloride (109 mg, 418 μmol) following method E to give the title compound (110 mg, 76%) as a white solid. $\delta_H$ (CD$_3$OD) 1.52–1.77 (m, 8H), 2.72–2.81 (m, 1H), 3.43–3.48 (m, 1H), 6.21–6.25 (m, 2H), 6.94 (d, 1H), 7.46 (d, 2H), 8.00 (d, 2H); m/z (ES$^-$) 430 [M−H]$^-$.

Example 28

N-[trans-4-(2,4-Dihydroxyphenyl)cyclohexyl]-4-fluorobenzenesulfonamide

From Preparation 35 (477 mg, 803 μmol) following method D to give the title compound (170 mg, 58%) as a white solid. $\delta_H$ ((CD$_3$)$_2$SO) 1.20–1.38 (m, 4H), 1.59–1.77 (m, 4H), 2.52–2.60 (m, 1H), 2.91–3.01 (br, 1H), 6.08 (dd, 1H), 6.19 (d, 1H), 6.73 (d, 1H), 7.37–7.44 (m, 2H), 7.70 (d, 1H), 7.83–7.90 (m, 2H), 8.86 (s, 1H), 8.97 (s, 1H); m/z (ES$^-$) 364 [M−H]$^-$.

Example 29

N-[trans-4-(2,4-Dihydroxyphenyl)cyclohexyl]-2,4-difluorobenzenesulfonamide

From Preparation 36 (450 mg, 739 μmol) following method D to give the title compound (180 mg, 64%) as a white solid. $\delta_H$ ((CD$_3$)$_2$SO) 1.20–1.39 (m, 4H), 1.57–1.72 (m, 4H), 2.52–2.60 (m, 1H), 3.00–3.11 (br, 1H), 6.18 (dd, 1H), 6.40 (d, 1H), 6.74 (d, 1H), 7.25 (m, 1H), 7.52 (m, 1H), 7.88 (m, 1H), 8.01 (d, 1H), 8.86 (s, 1H), 8.98 (s, 1H); m/z (ES$^-$) 382 [M−H]$^-$.

Example 30

N-[trans-4-(2,4-Dihydroxyphenyl)cyclohexyl]-2,3,4,5,6-pentafluorobenzenesulfonamide From Preparation 37 (450 mg, 675 μmol) following method D to give the title compound (207 mg, 70%) as a white solid. $\delta_H$ ((CD$_3$)$_2$SO) 1.27–1.41 (m, 4H), 1.60–1.83 (m, 4H), 2.54–2.61 (m, 1H), 3.16–3.25 (m, 1H), 6.09 (dd, 1H), 6.21 (d, 1H), 6.78 (d, 1H), 8.75 (d, 1H), 8.85 (s, 1H), 8.99 (s, 1H); m/z (ES$^-$) 436 [M−H]$^-$.

Example 31

N-[trans-4-(2,4-Dihydroxyphenyl)cyclohexyl]-3-(trifluoromethyl)benzenesulfonamide From Preparation 38 (516 mg, 801 μmol) following method D to give the title compound (240 mg, 72%) as a white solid. $\delta_H$ ((CD$_3$)$_2$SO) 1.22–1.41 (m, 4H), 1.60–1.79 (m, 4H), 2.52–2.62 (m, 1H), 3.01–3.14 (br, 1H), 6.13 (dd, 1H), 6.25 (d, 1H), 6.79 (d, 1H), 7.89 (t, 1H), 7.97 (d, 1H), 8.06 (d, 1H), 8.13–8.20 (m, 2H), 8.91 (s, 1H), 9.02 (s, 1H); m/z (ES$^-$) 414 [M–H]$^-$.

Example 32

N-[trans-4-(2,4-Dihydroxyphenyl)cyclohexyl]-3,5-bis(trifluoromethyl)benzenesulfonamide From Preparation 11 (200 mg, 459 μmol) and 3,5-bis(trifluoromethyl)benzene sulfonyl chloride (172 mg, 550 μmol) following method E to give the title compound (128 mg, 58%) as a white solid. $\delta_H$ ((CD$_3$)$_2$SO) 1.20–1.38 (m, 4H), 1.56–1.72 (m, 4H), 2.52–2.60 (m, 1H), 3.06–3.18 (br, 1H), 6.08 (dd, 1H), 6.39 (d, 1H), 6.72 (d, 1H), 8.10–8.16 (br, 1H), 8.39 (s, 2H), 8.44 (s, 1H), 8.84 (s, 1H), 8.97 (s, 1H); m/z (ES$^-$) 482 [M–H]$^-$.

Example 33

N-[cis-4-(2,4-Dihydroxyphenyl)cyclohexyl](phenyl)methanesulfonamide

From Preparation 12 (150 mg, 344 μmol) and 4-trifluoromethoxybenzenesulfonyl chloride (109 mg, 418 μmol) following method E to give the title compound (50 mg, 39%) as a white solid. $\delta_H$ (CD$_3$OD) 1.59–1.75 (m, 6H), 1.81–1.90 (m, 2H), 2.77–2.83 (m, 1H), 3.53–3.58 (br s, 1H), 4.36 (s, 2H), 6.23–6.28 (m, 2H), 6.95 (d, 1H), 7.34–7.40 (m, 3H), 7.43–7.48 (m, 2H); m/z (ES$^-$) 360 [M–H]$^-$.

Example 34

2-Chloro-N-[cis-4-(2,4-dihydroxyphenyl)cyclohexyl]-5-(trifluoromethyl)benzene sulfonamide Method F: 2-Chloro-5-trifluoromethylbenzenesulfonyl chloride (39 mg, 140 μmol) and DMAP (several crystals) were added to a stirred suspension of Preparation 12 (50 mg, 115 μmol) and morpholinomethyl polystyrene (85 mg of 3.4 μmol mg$^{-1}$ resin) in CH$_2$Cl$_2$ (4 ml), and the mixture was shaken for 24 hr. Polymer-bound tris(2-aminoethyl)amine (50 mg of 3.5 μmol mg$^{-1}$ resin) and NEt$_3$ (32 μl, 228 μmol) were added, and the reaction mixture agitated for 5 days. Filtration, washing with CH$_2$Cl$_2$, and solvent evaporation under reduced pressure gave the crude product, which was dissolved in MeOH (4 ml). The resulting solution was added to polymer-supported fluoride (200 mg of ca. 3 μmol mg$^{-1}$ resin), and the mixture was shaken at 20° C. for 4 days, before being filtered through a short SiO$_2$ pad. After washing with MeOH and HCl in Et$_2$O (2 M, 1 ml), the combined solutions were concentrated in vacuo to give the title compound (15 mg, 29%) as a white solid. $\delta_H$ (CD$_3$OD) 1.54–1.85 (m, 8H), 2.75–2.84 (m, 1H), 3.57–3.63 (br s, 1H), 6.24–6.29 (m, 2H), 6.97 (m, 1H), 7.84 (d, 1H), 7.91 (dd, 1H), 8.34 (d, 1H); m/z (ES$^-$) 448 [M–H]$^-$.

Example 35

3,5-Dichloro-N-[cis-4-(2,4-dihydroxyphenyl)cyclohexyl]benzenesulfonamide

From Preparation 12 (50 mg, 115 μmol) and 3,5-dichlorobenzenesulfonyl chloride (34 mg, 138 μmol) following method F to give the title compound (9 mg, 19%) as a white solid. $\delta_H$ (CD$_3$OD) 1.60–1.81 (m, 8H), 2.80–2.88 (m, 1H), 3.55 (s, 1H), 6.28–6.33 (m, 2H), 6.99 (d, 1H), 7.77 (t, 1H), 7.91 (d, 2H); m/z (ES$^-$) 414 [M–H]$^-$.

Example 36

4-Bromo-N-[cis-4-(2,4-dihydroxyphenyl)cyclohexyl]-2,5-difluorobenzenesulfonamide From Preparation 12 (50 mg, 115 μmol) and 4-bromo-2,5-difluorobenzenesulfonyl chloride (41 mg, 141 μmol) following method F to give the title compound (21 mg, 41%) as a white solid. $\delta_H$ (CD$_3$OD) 1.56–1.80 (m, 8H), 2.73–2.81 (m, 1H), 3.59 (s, 1H), 6.21–6.32 (m, 2H), 6.94 (d, 1H), 7.67–7.74 (m, 2H); m/z (ES$^-$) 461 [M–H]$^-$.

Example 37

N-[cis-4-(2,4-Dihydroxyphenyl)cyclohexyl]-3,5-bis(trifluoromethyl)benzenesulfonamide From Preparation 12 (50 mg, 115 μmol) and 3,5-bis(trifluoromethyl)benzenesulfonyl chloride (43 mg, 138 μmol) following method F to give the title compound (15 mg, 27%) as a white solid. $\delta_H$ (CD$_3$OD) 1.59–1.82 (m, 8H), 2.80–2.90 (m, 1H), 3.54 (s, 1H), 6.27–6.32 (m, 2H), 6.97 (d, 1H), 8.30 (s, 1H), 8.51 (s, 2H); m/z (ES$^-$) 482 [M–H]$^-$.

Example 38

N-[cis-4-(2,4-Dihydroxyphenyl)cyclohexyl]-1-naphthalenesulfonamide

From Preparation 12 (50 mg, 115 μmol) and 1-naphthalenesulfonyl chloride (31 mg, 137 μmol) following method F to give the title compound (17 mg, 37%) as a white solid. $\delta_H$ (CD$_3$OD) 1.31–1.72 (m, 8H), 2.68–2.78 (m, 1H), 3.51 (s, 1H), 6.20–6.26 (m, 2H), 6.71 (d, 1H), 7.60–7.80 (m, 3H), 8.07 (d, 1H), 8.19 (d, 1H), 8.29 (dd, 1H), 8.87 (d, 1H); m/z (ES$^+$) 398 [M+H]$^+$.

Example 39

N-[cis-4-(2,4-Dihydroxyphenyl)cyclohexyl]-3-(hydroxymethyl)benzenesulfonamide

Method G: A solution of LiAlH$_4$ in THF (1 M, 520 μl) was treated with a solution of Example 19 (20 mg, 49 μmol) in THF (8 ml). After 45 min, the reaction mixture was partitioned between aqueous HCl (1M, 15 ml) and EtOAc (15 ml). The aqueous phase was extracted with EtOAc (15 mL) and the combined organic extracts washed with aqueous NaHCO$_3$ (saturated, 15 ml), brine (15 ml), before being dried (MgSO$_4$). Filtration and solvent evaporation in vacuo provided the title compound (19 mg, quant.) as a white solid. $\delta_H$ ((CD$_3$)$_2$CO) 1.51–1.62 (m, 4H), 1.68–1.81 (m, 4H), 2.78–2.84 (m, 1H), 3.49–3.53 (m, 1H), 4.47 (t, 1H), 4.73 (d, 2H), 6.28 (dd, 1H), 6.35 (d, 1H), 6.57 (d, 1H), 6.98 (d, 1H), 7.50–7.60 (m, 2H), 7.78 (d, 1H), 7.90 (s, 1H), 7.93 (s, 1H), 8.00 (s, 1H); m/z (ES$^+$) 378 [M+H]$^+$.

Example 40

N-[cis-4-(2,4-Dihydroxyphenyl)cyclohexyl]-4-(hydroxymethyl)benzenesulfonamide

From Example 20 (16 mg, 40 μmol) following method G to give the title compound (11 mg, 73%) as a white solid. $\delta_H$ ((CD$_3$)$_2$CO)=1.52–1.63 (m, 4H), 1.66–1.80 (m, 4H), 2.78–2.84 (m, 1H), 3.48–3.54 (m, 1H), 4.34 (t, 1H), 4.73 (d, 2H), 6.28 (dd, 1H), 6.35 (d, 1H), 6.53 (d, 1H), 6.98 (d, 1H), 7.56 (d, 2H), 7.84–7.89 (m, 3H), 7.98 (s, 1H); m/z (ES$^+$) 378 [M+H]$^+$.

Example 41

4-({[cis-4-(2,4-Dihydroxyphenyl)cyclohexyl]amino}sulfonyl)benzoic acid

Method H: A solution of Example 20 (18 mg, 44 μmol) in THF-MeOH (3:1, 4 mL) was treated with a solution of LiOH.H$_2$O (12 mg, 286 μmol) in H$_2$O (2 ml). After stirring for 40 min, aqueous HCl (1 M, 500 μl) was added, and the mixture partitioned between H$_2$O (5 ml) and EtOAc (10 ml). The aqueous phase was extracted with EtOAc (5 ml) and the combined organic extracts were washed with brine (7 ml) and dried (MgSO$_4$). Filtration and solvent evaporation followed by RP-HPLC afforded the title compound (13 mg, 75%) as a white solid. δ$_H$ ((CD$_3$)$_2$CO) 1.47–1.80 (m, 8H), 2.77–2.86 (m, 1H), 3.52–3.60 (m, 1H), 6.27 (dd, 1H), 6.34 (d, 1H), 6.76 (d, 1H), 6.96 (d, 1H), 8.00 (d, 2H), 8.20 (d, 2H); m/z (ES$^-$) 390 [M−H]$^-$.

Example 42

3-({[cis-4-(2,4-Dihydroxyphenyl)cyclohexyl]amino}sulfonyl)benzoic acid

From Example 19 (107 mg, 264 μmol) following method H to give the title compound (50 mg, 48%) as a white solid. δ$_H$ ((CD$_3$)$_2$CO) 1.54–1.82 (m, 8H), 2.79–2.88 (m, 1H), 3.53–3.61 (m, 1H), 6.28 (dd, 1H), 6.35 (d, 1H), 6.80 (d, 1H), 6.97 (d, 1H), 7.75 (t, 1H), 7.84–8.08 (br, 2H), 8.14 (d, 1H), 8.25 (d, 1H), 8.55 (s, 1H); m/z (ES$^+$) 392 [M+H]$^+$.

Example 43

4-({[trans-4-(2,4-Dihydroxyphenyl)cyclohexyl]amino}sulfonyl)benzoic acid

From Example 22 (100 mg, 247 μmol) following method H to give the title compound (48 mg, 50%) as a white solid. δ$_H$ (CD$_3$OD) 1.28–1.44 (m, 4H), 1.71–1.82 (m, 4H), 2.64–2.72 (m, 1H), 3.06–3.16 (m, 1H), 6.16–6.24 (m, 2H), 6.81 (d, 1H), 7.97 (d, 2H), 8.17 (d, 2H); m/z (ES$^+$) 392 [M+H]$^+$.

Example 44

3-({[trans-4-(2,4-Dihydroxyphenyl)cyclohexyl]amino}sulfonyl)benzoic acid

From Example 21 (100 mg, 247 μmol) following method H to give the title compound (46 mg, 47%) as a white solid. δ$_H$ (CD$_3$OD) 1.30–1.48 (m, 4H), 1.75–1.90 (m, 4H), 2.68–2.77 (brs, 1H), 3.10–3.19 (m, 1H), 6.21–6.29 (m, 2H), 6.85 (d, 1H), 7.71 (t, 1H), 8.11 (d, 1H), 8.27 (d, 1H), 8.56 (s, 1H); m/z (ES$^+$) 392 [M+H]$^+$.

Example 45

Benzyl (2S)-2-{[3-({[cis-4-(2,4-dihydroxyphenyl)cyclohexyl]amino}sulfonyl)benzoyl]amino}-3-phenylpropanoate Method I: A solution of Example 42 (28 mg, 72 μmol) in DMF (1 ml) was treated with a solution of L-PheOBn.HOTs (35 mg, 82 μmol) in DMF (1.5 ml) and i-Pr$_2$NEt (45 μl, 258 μmol) before being cooled to 0° C. A solution of HATU (34 mg, 89 μmol) in DMF (1.5 ml) was added, and the reaction mixture allowed to warm to 20° C. over 3 days. Following concentration in vacuo, the residue was partitioned between EtOAc (10 ml) and H$_2$O (10 ml). The aqueous phase was extracted with EtOAc (5 ml) and the combined organic extracts were washed with aqueous HCl (2M, 2×15 ml), H$_2$O (15 ml), aqueous NaHCO$_3$ (saturated, 2×15 ml), and brine (15 ml), before being dried (MgSO$_4$). Filtration and solvent evaporation gave the crude product which was purified by RP-HPLC to give the title compound (13 mg, 29%) as a white solid. δ$_H$ ((CD$_3$)$_2$CO) 1.51–1.63 (m, 4H), 1.66–1.80 (m, 4H), 2.79–2.85 (m, 1H), 3.15–3.22 (m, 1H), 3.28–3.35 (m, 1H), 3.49–3.55 (m, 1H), 4.94–5.01 (m, 1H), 5.16–5.19 (m, 2H), 6.29 (dd, 1H), 6.35 (d, 1H), 6.71 (d, 1H), 6.97 (d, 1H), 7.18–7.37 (m, 10H), 7.67 (t, 1H), 7.89 (s, 1H), 8.00 (s, 1H), 8.02–8.06 (m, 2H), 8.25 (d, 1H), 8.33 (s, 1H); m/z (ES$^-$) 627 [M−H]$^-$.

Example 46

(2S)-2-{[3-({[cis-4-(2,4-Dihydroxyphenyl)cyclohexyl]amino}sulfonyl)benzoyl]amino}-3-phenylpropanoic acid Method J: A suspension of Example 45 (5.1 mg, 8.1 μmol) and Pd (10% on C, 5.6 mg) in i-PrOH (3 ml) was placed under a H$_2$ atmosphere, and stirred at 20° C. After 3 days, EtOAc (10 ml) was added and the mixture was filtered through Celite, subsequently washing with EtOAc (10 ml). Solvent evaporation in vacuo provided the title compound (4.0 mg, 91%) as a white solid. δ$_H$ ((CD$_3$)$_2$CO) 1.51–1.63 (m, 4H), 1.68–1.80 (m, 4H), 2.78–2.85 (m, 1H), 3.15–3.20 (m, 1H), 3.34–3.40 (m, 1H), 3.49–3.58 (m, 1H), 4.90–4.99 (m, 1H), 6.28 (dd, 1H), 6.35 (d, 1H), 6.71 (d, 1H), 6.97 (d, 1H), 7.19 (t, 1H), 7.27 (t, 2H), 7.35 (d, 2H), 7.66 (t, 1H), 7.85–7.91 (m, 2H), 8.03 (s, 1H), 8.05 (s, 1H), 8.10 (d, 1H), 8.33 (s, 1H); m/z (ES$^-$) 538 [M−H]$^-$.

Example 47

Benzyl 3-{[3-({[cis-4-(2,4-dihydroxyphenyl)cyclohexyl]amino}sulfonyl)benzoyl]amino}propanoate From Example 42 (43 mg, 110 μmol) and βAlaOBn.HOTs (43 mg, 121 μmol) following method I to give the title compound (8 mg, 13%) as a white solid. δ$_H$ ((CD$_3$)$_2$CO) 1.53–1.64 (m, 4H), 1.70–1.80 (m, 4H), 2.75 (t, 2H), 2.78–2.84 (m, 1H), 3.50–3.57 (m, 1H), 3.69–3.74 (m, 2H), 5.13 (s, 2H), 6.28 (dd, 1H), 6.35 (d, 1H), 6.71 (d, 1H), 6.96 (d, 1H), 7.27–7.39 (m, 5H), 7.67 (t, 1H), 7.91 (s, 1H), 8.01–8.16 (m, 4H), 8.37 (s, 1H); m/z (ES$^-$) 551 [M−H]$^-$.

Example 48

N-[3-({[cis-4-(2,4-Dihydroxyphenyl)cyclohexyl]amino}sulfonyl)benzoyl]-β-alanine

From Example 47 (9.3 mg, 16.8 μmol) following method J to give the title compound (5.6 mg, 72%) as a white solid. δ$_H$ ((CD$_3$)$_2$CO) 1.51–1.65 (m, 4H), 1.69–1.79 (m, 4H), 2.68 (t, 2H), 2.77–2.83 (m, 1H), 3.50–3.57 (m, 1H), 3.63–3.70 (m, 2H), 6.28 (dd, 1H), 6.35 (d, 1H), 6.70 (d, 1H), 6.97 (d, 1H), 7.68 (t, 1H), 7.80–7.95 (br, 1H), 8.02–8.12 (m, 3H), 8.37 (s, 1H); m/z (ES$^-$) 461 [M−H]$^-$.

Example 49

N-[cis-4-(2,4-Dihydroxyphenyl)cyclohexyl]-4-(hydrazinocarbonyl)benzenesulfonamide A solution of Example 20 (16 mg, 39 μmol) and N$_2$H$_4$.H$_2$O (79 μl, 1624 μmol) in MeOH-EtOH (1:4, 2.5 ml)

was heated under reflux for 24 hr. On cooling to 20° C., MeOH (15 ml) was added and the solution filtered. Solvent evaporation furnished the title compound (16 mg, quant) as a white solid. $\delta_H$ (CD$_3$OD) 1.56–1.80 (m, 8H), 2.77–2.83 (m, 1H), 3.46–3.52 (m, 1H), 6.26–6.30 (m, 2H), 6.98 (m, 1H), 7.98 (d, 2H), 8.02 (d, 2H); m/z (ES$^+$) 406 [M+H]$^+$.

Example 50

N-[cis-4-(2,4-Dihydroxyphenyl)cyclohexyl]-3-(1H-tetrazol-5-yl)benzenesulfonamide A solution of Example 9 (20 mg, 54 μmol) in DMF (2 ml) was treated with NH$_4$Cl (17 mg, 323 μmol) and NaN$_3$ (21 mg, 323 μmol). The mixture was heated under reflux for 6 hr, then stirred for 18 hr at 20° C., before being partitioned between EtOAc (30 ml) and H$_2$O (5 ml). The aqueous phase was extracted with EtOAc (3×15 ml) and the combined organic extracts were washed with brine (30 ml) and dried (MgSO$_4$). Filtration, solvent evaporation under reduced pressure, and FCC (EtOH-EtOAc, 1:3) afforded the title compound (16 mg, 72%) as a pale yellow solid. $\delta_H$ ((CD$_3$)$_2$CO) 1.30–1.88 (m, 8H), 2.60–2.71 (m, 1H), 3.62–3.69 (m, 1H), 4.23–4.30 (m, 1H), 6.20 (dd, 1H), 6.44 (d, 1H), 6.50 (d, 1H), 6.87 (d, 1H), 7.55 (t, 1H), 7.63–7.68 (m, 1H), 7.72–7.76 (m, 1H), 7.80 (d, 1H), 8.30 (d, 1H), 8.73 (s, 1H); m/z (ES$^-$) 414 [M−H]$^-$.

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

What is claimed is:

1. A method of lightening skin in a human, comprising administering to said human a skin-lightening effective amount of a compound of formula I:

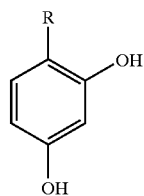

I or a pharmaceutically acceptable salt thereof, wherein:
R is a (C$_3$–C$_8$)cycloalkyl ring substituted by one of —N(R$^1$)SO$_2$(CHR$^1$)$_n$R$^2$ or —(C$_1$–C$_6$)alkylN(R$^1$)SO$_2$(CHR$^1$)$_n$R$^2$, wherein each R$^1$ is independently selected from hydrogen or (C$_1$–C$_6$)alkyl, R$^2$ is phenyl or naphthyl optionally substituted with one or more substituents independently selected from halogen, OH, —(C$_1$–C$_6$)alkyl, —(C$_1$–C$_6$)alkoxy, trifluoromethoxy, —S(O)$_m$(C$_1$–C$_6$)alkyl, amino, —N(R$^1$)CO(C$_1$–C$_6$)alkyl, COOR$^1$, —(C$_1$–C$_6$)alkylCOOR$^1$, —CO(C$_1$–C$_6$)alkyl, —(C$_1$–C$_6$)alkylOH, —(C$_1$–C$_6$)alkylamino, di-((C$_1$–C$_6$)alkyl)amino, nitro, cyano, —CONH(CHR$^1$)$_n$CO$_2$R$^1$, —CONR$^1$N(R$^1$)$_2$, trifluoromethyl, aryl, heteroaryl, and heterocycloalkyl; n is an integer from 0 to 6; and m is an integer from 0 to 2.

2. The method of claim 1, wherein R is a cyclohexyl or cyclohexenyl ring which is substituted at the 3- or 4-position.

3. The method of claim 1, wherein R is a cyclohexyl ring which is substituted at the 4-position.

4. The method of claim 1, wherein R is a cyclopentyl ring which is substituted at the 3-position.

5. The method of claim 1, wherein R is substituted by one of —(C$_1$–C$_6$)alkylN(R$^1$)SO$_2$(CHR$^1$)$_n$R$^2$.

6. The method of claim 1, wherein R is substituted by one of —N(R$^1$)SO$_2$(CHR$^1$)$_n$R$^2$.

7. A method of lightening skin in a human, comprising administering to said human a skin-lightening effective amount of a compound selected from the group consisting of:

N-[cis-4-(2,4-Dihydroxyphenyl)cyclohexyl] benzenesulfonamide;

4-Chloro-N-[cis-4-(2,4-dihydroxyphenyl)cyclohexyl] benzenesulfonamide;

3-Chloro-N-[cis-4-(2,4-dihydroxyphenyl)cyclohexyl]-4-fluorobenzenesulfonamide;

N-[cis-4-(2,4-Dihydroxyphenyl)cyclohexyl]-3-nitrobenzenesulfonamide;

N-[cis-4-(2,4-Dihydroxyphenyl)cyclohexyl]-4-nitrobenzenesulfonamide;

N-[cis-4-(2,4-Dihydroxyphenyl)cyclohexyl]-2,4-dinitrobenzenesulfonamide;

3-Cyano-N-[cis-4-(2,4-dihydroxyphenyl)cyclohexyl] benzenesulfonamide;

N-[cis-4-(2,4-Dihydroxyphenyl)cyclohexyl]-4-(methylsulfonyl)benzenesulfonamide;

N-[trans-4-(2,4-Dihydroxyphenyl)cyclohexyl] benzenesulfonamide;

N-[cis-4-(2,4-Dihydroxyphenyl)cyclohexyl]-2-naphthalenesulfonamide;

N-[cis-4-(2,4-Dihydroxyphenyl)cyclohexyl]-4-methylbenzenesulfonamide;

N-[trans-4-(2,4-Dihydroxyphenyl)cyclohexyl]-4-methylbenzenesulfonamide;

N-[cis-4 (2,4-Dihydroxyphenyl)cyclohexyl]-4-methoxybenzenesulfonamide;

N-[cis-4-(2,4-Dihydroxyphenyl)cyclohexyl]-5-(dimethylamino)-1-naphthalenesulfonamide;

Methyl 3-({[cis-4-(2,4-dihydroxyphenyl)cyclohexyl] amino}sulfonyl)benzoate;

Methyl 4-({[cis-4-(2,4-dihydroxyphenyl)cyclohexyl] amino}sulfonyl)benzoate;

Methyl 3-({[trans-4-(2,4-dihydroxyphenyl)cyclohexyl] amino}sulfonyl)benzoate;

Methyl 4-({[trans-4-(2,4-dihydroxyphenyl)cyclohexyl] amino}sulfonyl)benzoate;

4-Cyano-N-[trans-4-(2,4-dihydroxyphenyl)cyclohexyl] benzenesulfonamide;

N-[2-Chloro-4-({[cis-4-(2,4-dihydroxyphenyl) cyclohexyl]amino}sulfonyl)phenyl]acetamide;

4-Amino-3-chloro-N-[cis-4-(2,4-dihydroxyphenyl) cyclohexyl]benzenesulfonamide;

4-Acetyl-N-[cis-4-(2,4-dihydroxyphenyl)cyclohexyl] benzenesulfonamide;

N-[cis-4-(2,4-Dihydroxyphenyl)cyclohexyl]-4-(trifluoromethoxy)benzenesulfonamide;

N-[trans-4-(2,4-Dihydroxyphenyl)cyclohexyl]-4-fluorobenzenesulfonamide;

N-[trans-4-(2,4-Dihydroxyphenyl)cyclohexyl]-2,4-difluorobenzenesulfonamide;

N-[trans-4-(2,4-Dihydroxyphenyl)cyclohexyl]-2,3,4,5,6-pentafluorobenzene sulfonamide;

N-[trans-4-(2,4-Dihydroxyphenyl)cyclohexyl]-3-(trifluoromethyl)benzenesulfonamide;

N-[trans-4-(2,4-Dihydroxyphenylcyclohexyl]-3,5-bis(trifluoromethyl)benzenesulfonamide;

N-[cis-4-(2,4-Dihydroxyphenyl)cyclohexyl](phenyl)methanesulfonamide;

2-Chloro-N-[cis-4-(2,4-dihydroxyphenyl)cyclohexyl]-5-(trifluoromethyl)benzenesulfonamide;

3,5-Dichloro-N-[cis-4-(2,4-dihydroxyphenyl)cyclohexyl]benzenesulfonamide;

4-Bromo-N-[cis-4-(2,4-dihydroxyphenyl)cyclohexyl]-2,5-difluorobenzenesulfonamide;

N-[cis-4-(2,4-Dihydroxyphenyl)cyclohexyl]-3,5-bis(trifluoromethyl)benzenesulfonamide;

N-[cis-4-(2,4-Dihydroxyphenyl)cyclohexyl]-1-naphthalenesulfonamide;

N-[cis-4-(2,4-Dihydroxyphenyl)cyclohexyl]-3-(hydroxymethyl)benzenesulfonamide;

N-[cis-4-(2,4-Dihydroxyphenyl)cyclohexyl]-4-(hydroxymethyl)benzenesulfonamide;

4-({[cis-4-(2,4-Dihydroxyphenyl)cyclohexyl]amino}sulfonyl)benzoic acid;

3-({[cis-4-(2,4-Dihydroxyphenyl)cyclohexyl]amino}sulfonyl)benzoic acid;

4-({[trans-4-(2,4-Dihydroxyphenyl)cyclohexyl]amino}sulfonyl)benzoic acid;

3-({[trans-4-(2,4-Dihydroxyphenyl)cyclohexyl]amino}sulfonyl)benzoic acid;

N-[3-({[cis-4-(2,4-Dihydroxyphenyl)cyclohexyl]amino}sulfonyl)benzoyl]-β-alanine;

N-[cis-4-(2,4-Dihydroxyphenyl)cyclohexyl]-4-hydrazinocarbonyl)benzenesulfonamide;

N-[cis-4-(2,4-Dihydroxyphenyl)cyclohexyl]-3-(1H-tetrazol-5-yl)benzenesulfonamide; and a pharmaceutically acceptable salt thereof.

8. The method of claim 1, wherein the skin-lightening effective amount of the compound of formula I or pharmaceutically acceptable salt thereof is an amount that is effective at inhibiting tyrosinase in a human.

9. The method of claim 1, wherein the compound of formula I, or a pharmaceutically acceptable salt thereof, is applied topically.

* * * * *

UNITED STATES PATENT AND TRADEMARK OFFICE
CERTIFICATE OF CORRECTION

PATENT NO. : 6,852,747 B2
DATED : February 8, 2005
INVENTOR(S) : Stuart E. Bradley et al.

It is certified that error appears in the above-identified patent and that said Letters Patent is hereby corrected as shown below:

Title page,
Item [75], Inventors, "P. Sambrook Smith, Kenilworth, (GB)" should read
-- Colin P. Sambrook Smith, Kenilworth, (GB) --.
Item [56], References Cited, OTHER PUBLICATIONS, "Clare Gardner, et al."
reference, "Human adn Mouse PDE7B, a Novel cAMP-Specific Cyclic" should read
-- Human and Mouse PDE7B, a Novel camp-Specific Cyclic --.
"Ping Han, et al." reference, "Human Skeletal Muscle and Heart, J. Biol. Chem., Jun. 6," should read -- Human Skeletal Muscle and Heart, J. Biol. Chem., Jun. 27, --.

Column 50,
Line 1, "The method of claim 1, wherein R is a cyclohexyl or" should read -- The method of claim 1, wherein R is a cyclohexy --.
Line 2, "cyclohexenyl ring which is substituted at the 3- or" should read -- ring which is substituted at the 3- or --.
Line 42, "N-[cis-4 (2,4-Dihydroxyphenyl)cyclohexyl]-4-" should read
-- N-[cis-4-(2,4-Dihydroxyphenyl)cyclohexyl]-4- --.

Column 51,
Line 7, "N-[trans-4-(2,4-Dihydroxyphenylcyclohexyl]-3,5-bis" should read
-- N-[trans-4-(2,4-Dihydroxyphenyl)cyclohexyl]-3,5-bis --.

Signed and Sealed this

Twenty-third Day of August, 2005

JON W. DUDAS
*Director of the United States Patent and Trademark Office*